United States Patent
Hamilton

(10) Patent No.: US 10,854,332 B2
(45) Date of Patent: Dec. 1, 2020

(54) METHOD AND APPARATUS FOR PROVIDING CONTRACTION INFORMATION DURING LABOUR

(71) Applicant: Perigen Inc., Cary, NC (US)

(72) Inventor: Emily Hamilton, Quebec (CA)

(73) Assignee: PERIGEN, INC., Cary, NC (US)

( * ) Notice: Subject to any disclaimer, the term of this patent is extended or adjusted under 35 U.S.C. 154(b) by 839 days.

(21) Appl. No.: 15/625,409

(22) Filed: Jun. 16, 2017

(65) Prior Publication Data

US 2017/0286615 A1 Oct. 5, 2017

Related U.S. Application Data

(63) Continuation of application No. 11/716,496, filed on Mar. 9, 2007, now Pat. No. 9,805,164, which is a (Continued)

(51) Int. Cl.
*A61B 5/00* (2006.01)
*G16H 40/63* (2018.01)
(Continued)

(52) U.S. Cl.
CPC .......... *G16H 40/63* (2018.01); *A61B 5/0011* (2013.01); *A61B 5/02411* (2013.01);
(Continued)

(58) Field of Classification Search
CPC ........ G16H 40/63; G16H 40/67; G16H 40/60; A61B 5/0011; A61B 5/0444;
(Continued)

(56) References Cited

U.S. PATENT DOCUMENTS 3,989,034 A 11/1976 Hojaiban
5,042,503 A 8/1991 Torok et al.
(Continued)

FOREIGN PATENT DOCUMENTS

CA 2545339 7/2014
DE 27 41 344 A1 3/1979
(Continued)

OTHER PUBLICATIONS

Examiner's Report issued by the Canadian Intellectual Property Office in connection with Canadian patent application No. 2,970,898 dated Jun. 6, 2018—6 pages.
(Continued)

*Primary Examiner* — Eliza A Lam

(57) ABSTRACT

An apparatus for monitoring an obstetrics patient during labour is provided. The apparatus receives a contraction signal conveying information related to occurrences of uterine contractions over time and processes his signal to derive a sequence of rates of uterine contractions over time. The apparatus also implements a Graphical User Interface (GUI) presenting a tracing of at least part of the sequence of rates of uterine contractions over time along with a threshold rate of uterine contractions GUI is dynamically adapted over time based on the contraction signal received. The sequence of rates of uterine contractions derived over time is also processed to detect occurrences of anomalous contraction rates and to identify one or more portions of the tracing corresponding to sustained anomalous contraction rate segments during which anomalous contraction rates have persisted for time durations exceeding a pre-determined time duration. The GUI is configured to trigger an alarm event in response to identification of a specific sustained anomalous contraction rate segment.

38 Claims, 11 Drawing Sheets

Related U.S. Application Data continuation-in-part of application No. 11/416,281, filed on May 1, 2006, now Pat. No. 10,134,490.

(51) Int. Cl.
```
    A61B 5/024      (2006.01)
    G06F 19/00      (2018.01)
    G06Q 50/22      (2018.01)
    A61B 5/0444     (2006.01)
    A61B 8/02       (2006.01)
    A61B 8/08       (2006.01)
    G16H 40/67      (2018.01)
    A61B 5/03       (2006.01)
```

(52) U.S. Cl.
CPC .......... *A61B 5/0444* (2013.01); *A61B 5/4356* (2013.01); *A61B 5/4362* (2013.01); *A61B 5/742* (2013.01); *A61B 5/7445* (2013.01); *A61B 8/02* (2013.01); *A61B 8/0866* (2013.01); *G06F 19/00* (2013.01); *G06F 19/3418* (2013.01); *G06Q 50/22* (2013.01); *G16H 40/67* (2018.01); *A61B 5/033* (2013.01); *A61B 5/7435* (2013.01)

(58) Field of Classification Search
CPC ..... A61B 5/4356; A61B 5/4362; A61B 5/742; A61B 8/02; A61B 8/0866; A61B 5/02411; A61B 5/7445; A61B 5/033; A61B 5/7435; G06F 19/00; G06F 19/3418; G06Q 50/22
See application file for complete search history.

(56) References Cited

U.S. PATENT DOCUMENTS

| | | |
|---|---|---|
| 5,069,218 A | 12/1991 | Ikeda |
| 5,088,497 A | 2/1992 | Ikeda |
| 5,483,970 A | 1/1996 | Rosenberg |
| 6,200,279 B1 | 3/2001 | Paltieli |
| 6,254,537 B1 | 7/2001 | Nguyen |
| 6,423,016 B1 | 7/2002 | Hamilton et al. |
| 6,669,653 B2 | 12/2003 | Paltieli |
| 6,907,284 B2 | 6/2005 | Hamilton et al. |
| 7,113,819 B2 | 9/2006 | Hamilton et al. |
| 7,188,151 B2 | 3/2007 | Kumar et al. |
| 7,207,941 B2 | 4/2007 | Sharf |
| 8,870,793 B2 | 10/2014 | Hamilton |
| 2002/0083075 A1 | 6/2002 | Brummel et al. |
| 2002/0193670 A1 | 12/2002 | Garfield et al. |
| 2003/0187364 A1 | 10/2003 | Hamilton et al. |
| 2003/0208128 A1 | 11/2003 | Hamilton et al. |
| 2004/0133115 A1 | 7/2004 | Hamilton et al. |
| 2004/0254430 A1 | 12/2004 | Hamilton |
| 2005/0049509 A1 | 3/2005 | Mansour et al. |
| 2005/0267376 A1 | 12/2005 | Marossero et al. |
| 2006/0015036 A1 | 1/2006 | Paltieli |
| 2006/0282019 A1 | 12/2006 | Hamilton |
| 2007/0255588 A1 | 11/2007 | Hamilton |
| 2008/0039744 A1 | 2/2008 | Hamilton |
| 2009/0240158 A1 | 9/2009 | Hamilton et al. |
| 2009/0259133 A1 | 10/2009 | Wolfberg et al. |

FOREIGN PATENT DOCUMENTS

| | | |
|---|---|---|
| DE | 37 29 760 A1 | 3/1989 |
| DE | 198 22 250 A1 | 11/1999 |
| EP | 0286731 A1 | 10/1988 |
| EP | 0 306 915 A1 | 3/1989 |
| EP | 0 808 603 A2 | 11/1997 |
| EP | 1 161 921 A2 | 12/2001 |
| EP | 1 852 065 A1 | 11/2007 |
| EP | 1 852 065 B1 | 9/2011 |
| EP | 1 852 060 B1 | 12/2013 |
| WO | 01/93752 A2 | 12/2001 |
| WO | 2004/041059 A2 | 5/2004 |
| WO | 2005/015451 A1 | 2/2005 |

OTHER PUBLICATIONS

Notice of Allowance dated Jun. 20, 2018 in connection with U.S. Appl. No. 11/416,281—17 pages.
Henriksen K., Battles JB, Marks ET, et al., "Diagnosing Diagnosis Errors: Lessons from a Multi-institutional Collaborative Project", Advances in Patient Safety: From Research to Implementation, vol. 2: Concepts and Methodology, Feb. 2005, 21 pages.
Nunes .I, Ayres-de-Campos D., "Computer analysis of foetal monitoring signals", Best Practice and Research Clinical Obstetrics and Gynaecology (2015), http://dx.doi.org/10.1016/j.bpobgyn.2015.02.009, pp. 1 to 11.
Simpson et al., "Patient Safety Implications of Electronic Alerts and Alarms of Maternal-Fetal Status During Labor", Nursing for Women's Health (2016), vol. 20, Issue 4, pp. 358 to 366.
E. Hamilton, et al. "The Effect of Computer-Assisted Evaluation of Labor on Cesarean Rates", Journal of Healthcare Quality, vol. 26, Issue: 1, pp. 37-44, Feb. 1, 2004.
Declaration of Non-Establishment of International Search Report dated Jul. 5, 2006 in connection with International Patent Application No. (PCT/CA2006/000417), 2 pages.
Written Opinion of the International Searching Authority dated Jul. 5, 2006 in connection with International Patent Application No. PCT/CA2006/000417, 7 pages.
International Preliminary Report on Patentability dated Jun. 15, 2010 in connection with International Patent Application No. PCT/CA2008/002134, 6 pages.
International Search Report dated Mar. 30, 2009 in connection with International Patent Application No. PCT/CA2008/002134, 3 pages.
Written Opinion of the International Searching Authority dated Mar. 30, 2009 in connection with International Patent Application No. CA2008/002134, 4 pages.
Office Action issued by the United States Patent and Trademark Office dated Sep. 18, 2009 in connection with U.S. Appl. No. 11/416,281, 8 pages.
Office Action issued by the European Patent Office dated Jun. 2, 2008 in connection with EP Application No. 07 29 0544, 2 pages.
Office Action issued by the European Patent Office dated Jun. 3, 2008 in connection with EP Application No. 07 29 0533, 2 pages.
Office Action issued by the United States Patent and Trademark Office dated Mar. 18, 2010 in connection with U.S. Appl. No. 11/416,281, 18 pages.
Office Action issued by the United States Patent and Trademark Office dated Apr. 14, 2010 in connection with U.S. Appl. No. 11/716,496, 39 pages.
Office Action issued by the United States Patent and Trademark Office dated May 17, 2010 in connection with U.S Appl. No. 11/330,942, 7 pages.
Office Action issued by the United States Patent and Trademark Office dated Jul. 26, 2010 in connection with U.S. Appl. No. 11/330,942, 11 pages.
Office Action issued by the United States Patent and Trademark Office dated Dec. 21, 2010 in connection with U.S. Appl. No. 11/716,496, 36 Pages.
Office Action issued by the United States Patent and Trademark Office dated Feb. 7, 2011 in connection with U.S. Appl. No. 11/416,281, 23 Pages.
Office Action issued by the United States Patent and Trademark Office dated Feb. 7, 2011 in connection with U.S. Appl. No. 11/330,942, 11 Pages.
Office Action issued by the United States Patent and Trademark Office dated Mar. 1, 2011 in connection with U.S. Appl. No. 12/285,617, 7 Pages.
Office Action issued by the European Patent Office dated Feb. 23, 2011 in connection with European Patent Application No. 2007290544.1, 4 pages.

(56) References Cited

OTHER PUBLICATIONS

Notice of Allowance issued by the European Patent Office dated Mar. 24, 2011 in connection with European Patent Application No. 2007290533.4, 5 pages.
Office Action issued by the United States Patent and Trademark Office dated Oct. 3, 2011 in connection with U.S. Appl. No. 12/285,617, 6 Pages.
Office Action issued by the United States Patent and Trademark Office dated Apr. 5, 2012 in connection with U.S. Appl. No. 11/416,281, 22 Pages.
Examiner's Report (i.e. Office Action) issued by the Canadian Intellectual Property Office dated Jun. 8, 2012 in connection with Canadian Patent Application No. 2,610,393, 5 Pages.
Examiner's Report (i.e. Office Action) issued by the Canadian Intellectual Property Office dated Jul. 24, 2012 in connection with Canadian Patent Application No. 2,545,339, 3 Pages.
Office Action issued by the United States Patent and Trademark Office dated Feb. 4, 2013 in connection with U.S. Appl. No. 11/416,281, 16 Pages.
Office Action issued by the United States Patent and Trademark Office dated Mar. 18, 2013 in connection with U.S. Appl. No. 12/747,022, 13 pages.
Examiner's Report (i.e. Office Action) issued by the Canadian Intellectual Property Office dated May 3, 2013 in connection with Canadian Patent Application No. 2,610,393, 6 pages.
Office Action issued by the United States Patent and Trademark Office dated Jun. 11, 2013 in connection with U.S. Appl. No. 11/416,281, 17 Pages.
Office Action issued by the United States Patent and Trademark Office dated Jun. 19, 2013 in connection with U.S. Appl. No. 11/716,496, 37 pages.
Office Action issued by the United States Patent and Trademark Office dated Jun. 20, 2013 in connection with U.S. Appl. No. 12/747,022,16 pages.
Notice of Allowance issued by the European Patent Office dated Jul. 11, 2013 in connection with European Patent Application No. 2007290544.1, 5 pages.
Notice of Allowance issued by the United States Patent and Trademark Office dated Sep. 7, 2013 in connection with U.S. Appl. No. 11/330,942, 6 Pages.
Office Action issued by the United States Patent and Trademark Office dated Dec. 24, 2013 in connection with U.S. Appl. No. 11/416,281, 23 Pages.
Examiner's Report issued by the Canadian Intellectual Property Office dated Dec. 18, 2013 in connection with Canadian Patent Application No. 2,610,393, 8 pages.
Examiner's Report issued by the Canadian Intellectual Property Office dated Dec. 20, 2013 in connection with Canadian Patent Application No. 2,581,910, 8 pages.
Non-Final Office Action issued by the United States Patent and Trademark Office dated Apr. 2, 2014 in connection with U.S. Appl. No. 12/747,022, 15 pages.
Notice of Allowance issued by the United States Patent and Trademark Office dated Jul. 3, 2014 in connection with U.S. Appl. No. 14/036,188, 7 pages.
Examiner's Answer to Appeal Brief dated Sep. 25, 2014 in connection with U.S. Appl. No. 11/416,281, 25 pages.
Office Action issued by the United States Patent and Trademark Office dated Dec. 8, 2014 in connection with U.S. Appl. No. 12/747,022, 14 pages.

Examiner's Report issued by the Canadian Intellectual Property Office dated Dec. 18, 2014 in connection with Canadian Patent Application No. 2,581,910, 3 pages.
Examiner's Report issued by the Canadian Intellectual Property Office dated Jan. 26, 2015 in connection with Canadian Patent Application No. 2,707,312, 4 pages.
Examiner's Report issued by the Canadian Intellectual Property Office dated Feb. 27, 2015 in connection with Canadian Patent Application No. 2,640,855, 3 pages.
Notice of Allowance issued by the Canadian Intellectual Property Office dated Sep. 30, 2015 in connection with Canadian Patent Application No. 2,581,910, 1 page.
Examiner's Answer to Appeal Brief dated Nov. 19, 2015 in connection with U.S. Appl. No. 12/747,022, 17 pages.
Examiner's Report issued by the Canadian Intellectual Property Office dated Feb. 9, 2016 in connection with Canadian Patent Application No. 2,640,855, 3 pages.
Notice of Allowance issued by the Canadian Intellectual Property Office dated Feb. 8, 2016 in connection with Canadian Patent Application No. 2,707,312, 1 page.
Board Decision dated Dec. 21, 2016 in connection with U.S. Appl. No. 11/416,281, 9 pages.
Board Decision dated Dec. 29, 2016 in connection with U.S. Appl. No. 11/716,496, 8 pages.
Examiner's Report (Final Action) issued by the Canadian Intellectual Property Office dated Dec. 19, 2016 in connection with Canadian Patent Application No. 2,610,393, 5 pages.
Canadian Patent No. 2,640,855 issued on Jan. 3, 2017, 39 pages.
Office Action issued by the United States Patent and Trademark Office dated May 1, 2017 in connection with U.S. Appl. No. 11/716,496, 25 pages.
E. Hamilton, E. Wright, "Labor Pains, Unraveling the Complexity of OB Decision Making", Crit Care Nurs Q, 2006, vol. 29, No. 4, pp. 342-353.
Patent Trial and Appeal Board (PTAB) decision dated Sep. 1, 2017 in connection with U.S. Appl. No. 12/747,022.
Notice of Allowance dated Jun. 19, 2017 in connection with U.S. Appl. No. 11/716,496.
Final Office Action dated Jul. 17, 2017 in connection with U.S. Appl. No. 11/416,281—18 pages.
Hamilton, E. et al., "A comprehensive labour surveillance system", Journal of Perinatal Medicine, vol. 15, Supplement 1, p. 144 (1987).
World Health Organisation Partograph in management of labour, The Lancet, vol. 343, Jun. 4, 1994, pp. 1399-1404.
World Health Organisation, Division of Family Health, Geneva, Maternal Health and Safe Motherhood Programme, "The Partograph: The Application of the WHO Partograph in the Management of Labour", Copyright World Health Organisation, Geneva, Switzerland, 1994, pp. i-xviii and pp. 1-7.
Zhang, Jun et al. 'Reassessing the Labor Curve in nulliparous women', AJOG (2002), vol. 187, No. 4, pp. 824-828.
Sallam et al., "Mathematical relationships between uterine contractions, cervical dilatation, descent and rotation in spontaneous vertex deliveries", International Journal of Gynecology & Obstetrics, vol. 64, Issue 2, Feb. 1, 1999 (Feb. 1, 1999), pp. 135-139.
Emanuel A. Friedman, M.D., "Graphic analysis of labor", American Journal of Obstetrics & Gynecology, vol. 68, 1954, pp. 1568-1575.
European Search Report dated Jul. 25, 2007 in connection with EP Patent Application No. 07 29 0544, 7 pages.
European Search Report dated Jul. 25, 2017 in connection with EP Patent Application No. 07 29 0533, 7 pages.

METHOD AND APPARATUS FOR PROVIDING CONTRACTION INFORMATION DURING LABOUR

CROSS-REFERENCE TO RELATED APPLICATIONS

This application is a continuation claiming the benefit of priority under 35 USC § 120 based on of U.S. patent application Ser. No. 11/716,496 filed Mar. 9, 2007 and presently pending, which was a continuation-in-part application of previously filed U.S. application entitled "METHOD AND APPARATUS FOR DISPLAYING LABOUR RELATED INFORMATION ASSOCIATED TO AN OBSTETRICS PATIENT" filed on May 1, 2006 by Emily Hamilton and which was assigned Ser. No. 11/416,281. The contents of the above applications are incorporated herein by reference.

FIELD OF THE INVENTION

The present invention relates generally to the field of obstetrics and, more specifically, to a method and apparatus for monitoring labor progression and for providing a user interface to display data conveying maternal information during labor.

BACKGROUND

Uterine contractions are intermittent and co-ordinated tightenings of the uterine muscle. Uterine contractions provide the force that makes labour progress, by causing the baby to descend through the birth canal and making the cervix efface (shorten), and dilate (open). This force is related to the frequency, strength and duration of the contractions. Oxytocin is a natural hormone that causes uterine contractions. A synthetic version of oxytocin is often administered during labour to increase the frequency, duration and strength of uterine contractions or to induce labour. The medication is administered through a continuous intravenous infusion. There is no fixed dosage as in antibiotic therapy; rather the dose is adjusted frequently according to the patient's response to achieve the desired frequency and intensity of contractions.

When the uterine muscle contracts, the maternal blood vessels in it are constricted causing a temporary reduction in the blood flow and delivery of oxygen to the baby's placenta. Relaxation of the contraction restores the flow and oxygen delivery to the baby. In normal circumstances, babies tolerate contractions well. However, in other circumstances, such as when the placenta malfunctions or the contractions are excessively frequent with little or no relaxation time between them, the baby may not tolerate this reduction in oxygen delivery. If the situation remains uncorrected or worsens it may result in injury to the baby's brain and permanent disability.

At present, clinical staff estimates the frequency of contractions by feeling the mother's abdomen for a few minutes and noting the timing of a few contractions or by examining a paper tracing that shows a recording of contraction pressures/intensity over time. These assessments are performed periodically and the results recorded in the medical record.

A deficiency with the above-described methods for assessing contraction frequency is that they are prone to inaccuracy and incompleteness because they are visual estimates based on short selected segments of the tracing and the caregiver may fail to make assessments at the prescribed time intervals and may fail to appreciate the degree and duration of the abnormality as well as the response of the baby. Thus, there can be a delay or failure to recognize overly frequent contractions, to adjust the medication correctly, resulting in an iatrogenic injury to the baby.

In the context of the above, there is a need to provide a method and device for monitoring contractions for an obstetrics patient that alleviates at least in part problems associated with the existing methods and devices.

SUMMARY

In accordance with a first aspect, a computer readable storage medium storing a program element is provided suitable for execution by a CPU where the program element implements a graphical user interface module for displaying uterine contraction information. The graphical user interface module is adapted for receiving a contraction signal conveying information related to occurrences of uterine contractions over time. The graphical user interface module is adapted for displaying first information conveying a rate of uterine contractions, the first information being derived at least in part on the basis of at least a portion of the contraction signal. The graphical user interface module is also adapted for displaying, concurrently with the first information, second information conveying a threshold rate of uterine contractions. The graphical user interface module is also adapted selectively causing an alarm event based at least in part on a rate of uterine contractions conveyed by the first information and the threshold rate of uterine contractions.

An advantage of some practical implementations is that they may allow clinical staff making use of the graphical user interface module to readily track contraction rates and be provided with an indication, through the display of the threshold rate of uterine contractions, of a boundary defining safe care. As such, the clinical staff is enabled to more easily assess labour progress. More specifically, the display of the graphical user interface module allows the clinical staff to readily ascertain when the contraction rate falls outside a limit set by the threshold rate of uterine contractions and, therefore, allows the clinical staff to take the necessary action in response to the occurrence of this event. In specific practical implementation, the threshold rate of uterine contractions will be set by hospital policy and/or on the basis of recognized best practices. The graphical user interface module also provides an improved method for alerting the staff to conditions requiring intervention by causing an alarm event.

In accordance with specific examples of implementation, the graphical user interface module may cause an alarm event in response to a rate of uterine contractions conveyed by the first information falling outside a limit set by the threshold rate of uterine contractions. Alternatively, the graphical user interface module may cause an alarm event in response to a rate of uterine contractions conveyed by the first information exceeding the threshold rate of uterine contractions. Alternatively, the graphical user interface module may cause an alarm event in response to a rate of uterine contractions conveyed by the first information falling outside a limit set by the threshold rate of uterine contractions for a time duration exceeding a predetermined time duration. Advantageously, this second alternative allows the graphical user interface module to take into account a prolonged duration of an anomalous contraction rate when causing an alarm event.

In accordance with specific examples of implementation, the graphical user interface module receives contraction medication information conveying information associated to administration of contraction inducing medication to the obstetrics patient. The contraction medication information may indicate whether contraction-inducing medication was administered and, optionally, a dosage of the contraction inducing medication administered. The graphical user interface module selectively causes an alarm event based at least in part on a rate of uterine contractions conveyed by the first information, on the threshold rate of uterine contractions and on the contraction medication information.

Advantageously, this alternative implementation allows the graphical user interface module to take into account whether contraction inducing medication was administered to the obstetrics patient being monitored (and optionally the amount of contraction inducing medication which was administered) when causing an alarm event.

In accordance with other specific examples of implementation, the graphical user interface module receives fetal heart rate information. The graphical user interface module selectively causes an alarm event based at least in part on a rate of uterine contractions conveyed by the first information, on the threshold rate of uterine contractions and on the fetal heart rate information. The fetal heart rate information may including a fetal heart rate signal or, alternatively, may include information conveying a level of risk associated with the fetus, the level of risk being derived on the basis of a fetal heart rate signal. Where the fetal heart rate information includes a fetal heart rate signal, the graphical user interface module is adapted for processing the signal to determine a level of risk associated with the fetal heart rate signal. Any suitable method for assessing a level of risk on the basis of a fetal heart rate signal may be used. For example, the level of risk may be based on the frequency of the fetal heart rate, whether it is too high or too low for a certain period of time. Alternatively, the level of risk may be based on other suitable known methods. A non-limiting example of a method for providing an indication of the level of risk is described in U.S. Pat. No. 7,113,819, entitled "Method and apparatus for monitoring the condition of a fetus", issued on Sep. 26, 2006 to E. Hamilton et al. and assigned to LMS Medical Systems Ltd. The contents of this document are incorporated herein by reference. Other suitable methods for assessing a level of risk on the basis of a fetal heart rate signal may be used without detracting from the spirit of the invention.

Advantageously, the above-described alternative implementation may allow the graphical user interface module to take into account the behaviour of the fetal heart rate, and therefore the response of the baby, in combination with the contraction rate when causing an alarm event.

In accordance with other specific examples of implementation, the graphical user interface module receives fetal heart rate information and contraction medication information. The graphical user interface module selectively causes an alarm event based at least in part on a rate of uterine contractions conveyed by the first information, on the threshold rate of uterine contractions, on the fetal heart rate information and on the contraction medication information.

In accordance with specific examples of implementation, the alarm event may include displaying a visual indicator, causing an audio signal to be issued and/or causing a message signal to be transmitted to a remote device. The remote device may be any device suitable for conveying information to its user. Examples of remote devices include, without being limited to, PDAs, telephones, pager and computing terminals.

In accordance with a first specific example of implementation, the first information includes a first tracing conveying rates of uterine contractions over time and the second information includes a second tracing conveying the threshold rate of uterine contractions. The first tracing and the second tracing are displayed in a same viewing window.

Advantageously, the first and second tracings displayed a same viewing window allow the clinical staff to readily ascertain the contraction rate and variations thereof over an extended time period. This allows the clinical staff to more easily distinguish between short-term variations in contraction rate, which could signal innocuous transient states and long term persistence and trends in the contraction rate. In addition, this allows the clinical staff to have a more complete view of the history of the contraction rate since labour onset, or at least since the clinical staff was monitoring the labour. For example, this allows determining whether the contraction rate is consistently above the threshold rate or whether it was merely a temporary increase in contraction rate and was induced either through the administration of medication or other method.

In accordance with a specific implementation, the graphical user interface module is operative for processing the contraction signal to derive a set of contraction rate data elements, each contraction rate data element being associated to a segment of the contraction signal. The graphical user interface module causes an alarm event in response to at least one contraction rate data element in the set of contraction rate data elements falling outside a limit set by the threshold rate.

In accordance with a second specific example of implementation, the first information and the second information include alphanumeric characters for conveying rates of uterine contractions over time and a threshold rate of uterine contractions.

In accordance with another aspect, a method is provided for displaying uterine contraction information. The method comprises receiving a contraction signal conveying information related to occurrences of uterine contractions over time. The method also comprises displaying first information conveying a rate of uterine contractions, the first information being derived at least in part on the basis of at least a portion of the contraction signal. The method also comprises displaying, concurrently with the first information, second information conveying a threshold rate of uterine contractions. The method also comprises selectively causing an alarm event based at least in part on a rate of uterine contractions conveyed by the first information and the threshold rate of uterine contractions.

In accordance with another aspect, an apparatus is provided for displaying uterine contraction information in accordance with the above-described method.

In accordance with another aspect, a labour monitoring system is provided. The system includes a sensor for receiving information indicative of occurrences of uterine contractions over time. The system also includes an apparatus for implementing a user interface for displaying uterine contraction information. The apparatus comprises an input in communication with the sensor for receiving a contraction signal conveying information related to occurrences of uterine contractions over time. The apparatus also comprises a processing unit in communication with the input. The processing unit implements a graphical user interface module for displaying uterine contraction information. The graphical user interface module is adapted for displaying first information conveying a rate of uterine contractions, the first information being derived at least in part on the basis of at least a portion of the contraction signal. The graphical user interface module is also adapted for displaying, concurrently with the first information, second information conveying a threshold rate of uterine contractions. The graphical user interface module is also adapted for selectively causing an alarm event based at least in part on a rate of uterine contractions conveyed by the first information and the threshold rate of uterine contractions. The apparatus includes an output in communication with the processing unit for releasing a signal for causing a display unit to display the graphical user interface module. The system also includes a display unit in communication with the output of the apparatus. The display unit is responsive to the signal releasing by the output of the apparatus to display the graphical user interface module.

In accordance with yet another aspect, a server system implementing a graphical user interface module is provided for displaying uterine contraction information. The server system stores a program element for execution by a CPU. The program element includes a plurality of program element components. A first program element component is for receiving a contraction signal conveying information related to occurrences of uterine contractions over time. A second program element component is for processing the contraction signal and issue a signal for displaying:

first information conveying a rate of uterine contractions, the first information being derived at least in part on the basis of at least a portion of the contraction signal; and displaying, concurrently with the first information, second information conveying a threshold rate of uterine contractions;

A third program element component is for selectively causing an alarm event based at least in part on a rate of uterine contractions conveyed by the first information and the threshold rate of uterine contractions.

In accordance with yet another aspect, a client-server system for implementing a graphical user interface module is provided for displaying uterine contraction information. The client-server system comprises a client system and a server system operative to exchange messages over a data network. The server system stores a program element for execution by a CPU. The program element includes a plurality of program element components. A first program element component is for execution on the server system and is for receiving a contraction signal conveying information related to occurrences of uterine contractions over time. A second program element component is for execution on the server system and is for sending messages to the client system for causing the client system to:

i) display first information conveying a rate of uterine contractions, the first information being derived at least in part on the basis of at least a portion of the contraction signal; and ii) display, concurrently with the first information, second information conveying a threshold rate of uterine contractions.

A third program element component is for execution on the server system and is for selectively sending messages to the client system for causing an alarm event based at least in part on a rate of uterine contractions conveyed by the first information and the threshold rate of uterine contractions.

In a specific implementation, the client-server system includes a plurality of client systems operative to exchange messages with the server system over a data network. The data network may be of any suitable network configuration including Intranets and the Internet.

In accordance with another aspect, an apparatus is provided for implementing a user interface for displaying uterine contraction information. The apparatus comprises means for receiving a contraction signal conveying information related to occurrences of uterine contractions over time and means for implementing a graphical user interface module for displaying uterine contraction information. The graphical user interface module is adapted for displaying first information conveying a rate of uterine contractions, the first information being derived at least in part on the basis of at least a portion of the contraction signal. The graphical user interface module is also adapted for displaying concurrently with the first information, second information conveying a threshold rate of uterine contractions. The graphical user interface module is also adapted for selectively causing an alarm event based at least in part on a rate of uterine contractions conveyed by the first information and the threshold rate of uterine contractions. The apparatus also includes means for releasing a signal for causing a display unit to display the graphical user interface module.

In accordance with yet another aspect, a method is provided for displaying uterine contraction information. The method comprises transmitting to a remote computing unit a contraction signal conveying information related to occurrences of uterine contractions over time. The method also comprises receiving first information conveying a rate of uterine contractions, the first information corresponding to at least a portion of the contraction signal. The method also comprises displaying a graphical user interface conveying the first information and a threshold rate of uterine contractions. The method also comprises receiving a signal suitable for causing an alarm event based at least in part on a rate of uterine contractions conveyed by the first information and the threshold rate of uterine contractions.

In accordance with another aspect, a computer readable storage medium storing a program element suitable for execution by a CPU is provided, the program element implementing a graphical user interface module for displaying uterine contraction information. The graphical user interface module is adapted for receiving a contraction signal conveying information related to uterine contractions over time. The graphical user interface module is also adapted for processing the contraction signal to derive first information conveying rates of uterine contractions over time and for displaying the first information in a viewing window. The graphical user interface module is also adapted for displaying concurrently with the first information, second information conveying a threshold rate of uterine contractions.

These and other aspects and features of the present invention will now become apparent to those of ordinary skill in the art upon review of the following description of specific embodiments of the invention in conjunction with the accompanying drawings.

Other aspects and features of the present invention will become apparent to those ordinarily skilled in the art upon review of the following description of specific embodiments of the invention in conjunction with the accompanying figures.

DETAILED DESCRIPTION

Figure 1:
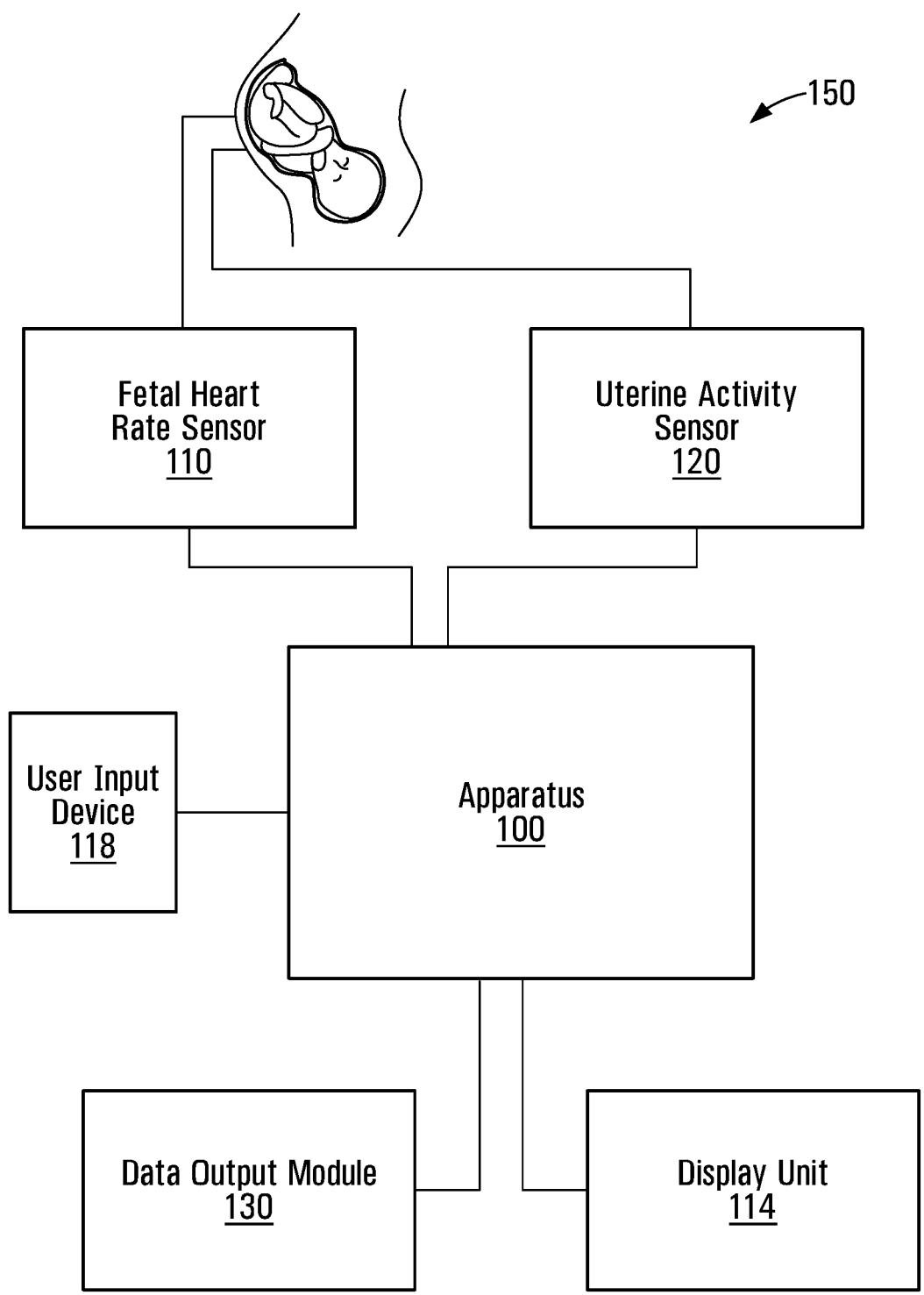
FIG. 1 shows a high-level functional block diagram of a labour monitoring system implementing a user interface for displaying uterine contraction information in accordance with a specific example of implementation of the present invention.

With reference to FIG. 1, there is shown a configuration of a labour monitoring system 150 comprising a uterine activity sensor 120, a user input device 118, an apparatus 100 implementing a user interface for displaying uterine contraction information and a display unit 114.

In accordance with a specific implementation, the sensor 120 for monitoring uterine activity samples the contraction pattern at a certain pre-determined frequency to generate a signal indicative of uterine activity. The resulting signal, herein referred to as a contraction signal, conveys information related to the occurrence of uterine contractions over time. More specifically, the contraction signal conveys information on the occurrence of contraction events. Broadly stated, a contraction event refers to a continuous time period during which the uterine muscle of an obstetrics patient is tightening. During labour, contraction events are interleaved with relaxation periods during which the uterine muscle ceases to contract or contracts to a lesser extent. The contraction signal may be a continuous signal conveying contraction intensity information or may be comprised of unitary signal events where a signal event is generated when a contraction event is detected. Typically, when the contraction signal is comprised of unitary signal events, a signal event is generated when the onset of a contraction event is detected. Sensors for monitoring uterine activity are well known in the art to which this invention pertains and any suitable sensor may be used without detracting from the spirit of the invention and as such will not be described further here.

Alternatively, certain embodiments of the labour monitoring system 150 may omit the sensor 120 and instead make use of a user-controlled input for generating the contraction signal. The user-controlled input allows a user to provide over time information signalling the onset of a contraction event such as to convey information associated to contraction activity over time. Such a user-controlled input may be in the form of a manually controlled actuator that can be activated by depressing a button when the obstetrics patient senses the onset of a contraction or in any other suitable configuration allowing a user to signal the onset of contraction events over time. Although the user controlling the actuator may be the expectant mother, it will most likely be a person other than the expectant mother, such as the expectant father or a nurse for example, since the expectant mother will most likely have other concerns during labour. In such an alternative embodiment, the contraction signal is comprised of unitary signal events. It will be readily appreciated that such a configuration may be somewhat inconvenient in practice since it would require that the user diligently enter contraction information. Consequently, although this alternative implementation has been presented for the purpose of completeness and as an alternative example of implementation, it will be readily appreciated that using a sensor 120 for monitoring uterine activity will be preferred in practical implementations of the invention.

The apparatus 100 is for implementing a graphical user interface module for displaying uterine contraction information. The graphical user interface module displays first information conveying a rate of uterine contractions derived at least in part on the basis of at least a portion of the contraction signal. The graphical user interface module also displays, concurrently with the first information, second information conveying a threshold rate of uterine contractions. The graphical user interface module selectively causes an alarm event based at least in part on a rate of uterine contractions conveyed by the first information and the threshold rate of uterine contractions. The apparatus 100 also releases a signal for causing the display unit 114 to display the graphical user interface module. Optionally, the apparatus is further adapted for releasing signals to a data output module 130 for causing the latter to convey information associated to labour progression to a user of the labour monitoring system 150. Specific examples of implementation of the apparatus 100 and of the graphical user interface module will be described later on in the specification.

The user input device 118 is for receiving data from a user of the system. The user input device 118 may be used, for example, to enter information associated with the obstetrics patient and/or to manipulate the information displayed by the user interface implemented by the apparatus 100. Optionally still, the user input device 118 may be used to enter contraction medication information conveying information associated to administration of contraction inducing medication to the obstetrics patient. The contraction medication information may indicate whether contraction-inducing medication was administered and, optionally, the dosage of the contraction inducing medication that was administered. Since, typically, contraction-inducing medication is administered continuously over time and not as a one shot dose, the contraction medication information conveys the dosage of the contraction inducing medication administered over time. The user input device 118 includes any one or a combination of the following: keyboard, pointing device, touch sensitive surface, keypad or speech recognition unit. Certain embodiments of the labour monitoring system 150 may omit the user input device 118 without detracting from the spirit of the invention.

Optionally, as shown in FIG. 1, the labour monitoring system 150 may further include a fetal heart rate sensor 110. The fetal heart rate sensor 110 is for detecting a fetal heart rate of a fetus in-utero, also referred to as a fetus in the womb. The fetal heart rate sensor 110 samples the fetal heart rate at a certain pre-determined frequency to generate the signal indicative of the fetal heart rate. Fetal heart rate sensors are well known in the art to which this invention pertains and any suitable sensor for detecting a fetal heart rate may be used without detracting from the spirit of the invention and as such will not be described further here.

Optionally still, the labour monitoring system 150 may include other sensors (not shown) for measuring labour progress and the fetus' tolerance to labour. Such sensors may include for example:
- a sensor for measuring the maternal oxygen saturation
- a sensor for measuring the fetal oxygen saturation
- a sensor for measuring maternal blood pressure
- a sensor for measuring and analysing the fetal electrocardiogram Such sensors are not critical to the invention and therefore will not be described further here.

The display unit 114 is in communication with the apparatus 100 and receives a signal causing the display unit 114 to display a graphical user interface module implemented by apparatus 100. The display unit 114 may be in the form of a display screen, a printer or any other suitable device for conveying to the physician or other health care professional uterine contraction information associated to an obstetrics patient.

Optionally, the labour monitoring system 150 may further include a data output module 130. The data output module 130 is in communication with the apparatus 100 and is suitable for receiving signals generated by the apparatus 100. In a first specific example of implementation, the data output module 130 includes an audio module for releasing audio signals on the basis of signals received from the apparatus 100. In a second specific example of implementation, the data output module 130 includes a data communication entity suitable for transmitting messages to remote devices causing the latter to convey to a user of the labour monitoring system 150 information associated to labour progression. Examples of remote devices include, without being limited to, PDAs, telephones, pagers and computing terminals.

A specific practical implementation of the labour monitoring system 150 may implement the graphical user interface module for displaying uterine contraction information as a stand-alone component or alternatively as part of a more complete labour monitoring system including a plurality of modules for monitoring various aspects of labour progression. An example of such a labour monitoring system is described in co-pending U.S. patent application entitled "METHOD AND APPARATUS FOR DISPLAYING LABOUR RELATED INFORMATION ASSOCIATED TO AN OBSTETRICS PATIENT" filed on May 1, 2006 by Emily Hamilton and which was assigned Ser. No. 11/416,281. The contents of the above application are incorporated herein by reference.

Apparatus 100

Figure 2:
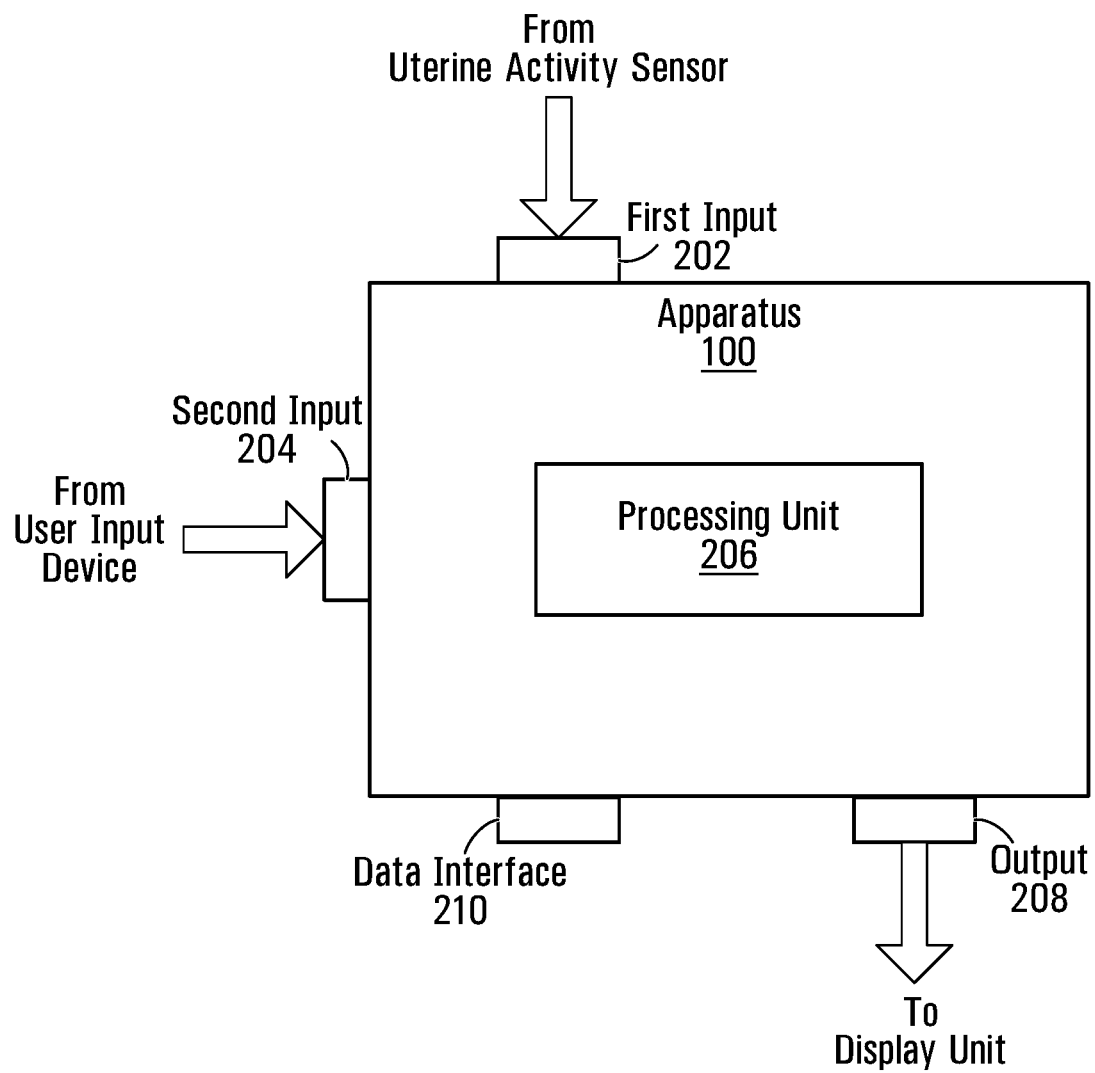
FIG. 2 is a functional block diagram of an apparatus implementing a user interface for displaying uterine contraction information in accordance with a specific example of implementation of the present invention.

A specific example of implementation of apparatus 100 will now be described with reference to FIG. 2. The apparatus 100 includes an input 202 (labelled as first input in the figure), a processing unit 206 and an output 208. The first input 202 is for receiving a contraction signal from the uterine activity sensor 120 (shown in FIG. 1) conveying information related to occurrences of uterine contractions over time. The processing unit 206 is in communication with the first input 202 and implements a graphical user interface module for displaying uterine contraction information. The output 208 is for releasing a signal for causing the display unit 114 (shown in FIG. 1) to display the graphical user interface module implemented by processing unit 206. Optionally, as shown in FIG. 2, the apparatus further includes a second input 216 for receiving data from a user through input device 118 (shown in FIG. 1). Optionally still, the apparatus further includes a data interface 210 for exchanging signals with a data output module 130 (shown in FIG. 1) for causing the latter to convey information associated to labour progression to a user of the labour monitoring system 150 (shown in FIG. 1).

Optionally, the apparatus further includes an additional input (not shown in the figures) for receiving fetal heart rate information. The fetal heart rate information may including a fetal heart rate signal as generated by fetal heart rate sensor (110) or, alternatively, may include information conveying a level of risk associated with the fetus, the level of risk being derived on the basis of a fetal heart rate signal. Where the fetal heart rate information includes a fetal heart rate signal, the apparatus 100 is adapted for processing the signal to determine a level of risk associated with the fetal heart rate signal. Any suitable method for assessing a level of risk on the basis of a fetal heart rate signal may be used. For example, the level of risk may be based on the frequency of the fetal heart rate, whether it is too high or too low for a certain period of time. Alternatively, the level of risk may be based on other known methods. A non-limiting example of a method for providing an indication of the level of risk is described in U.S. Pat. No. 7,113,819, entitled "Method and apparatus for monitoring the condition of a fetus", issued on Sep. 26, 2006 to E. Hamilton et al. and assigned to LMS Medical Systems Ltd. The contents of this document are incorporated herein by reference. Other suitable methods for assessing a level of risk on the basis of a fetal heart rate signal may be used without detracting from the spirit of the invention.

The graphical user interface module will now be described in greater detail.

The graphical user interface module receives the contraction signal conveying information related to uterine contractions over time and displays first and second information. The first information conveys a rate of uterine contractions which is derived at least in part on the basis of at least a portion of the contraction signal received at input 202. The second information conveys a threshold rate of uterine contractions. The threshold rate of uterine contractions defines boundaries of safe care and may be set in accordance best practices or in accordance with hospital/care-giver facility policy. Although the present description refers to a single threshold rate of uterine contraction, it will be readily apparent that embodiments including multiple thresholds of uterine contractions, each threshold being associated with a respective degree of risk to the obstetrics patient, may be used in alternative implementations of the present invention.

The specific manner in which the information can be displayed to a user of the system 150 by the graphical user interface module may vary from one implementation to the other without detracting from the spirit of the invention. Specific non-limiting examples of implementation of a graphical user interface module are shown in FIGS. 3, 4a and 4b.

Figure 3:
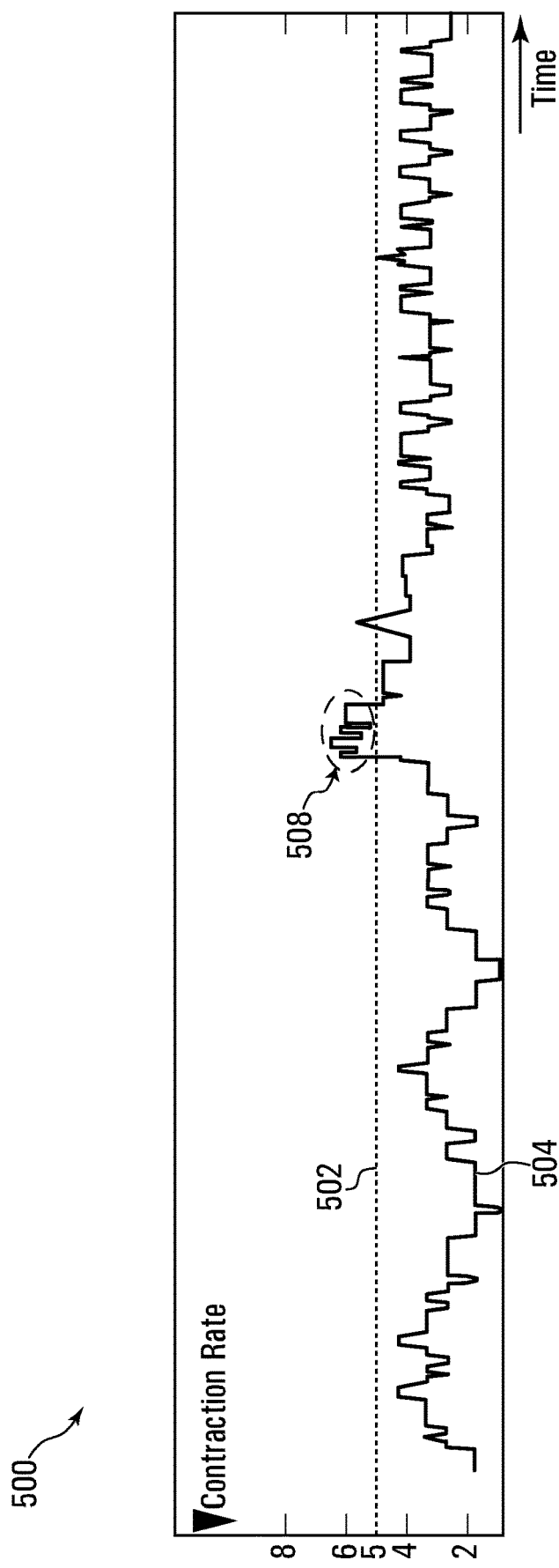
FIG. 3 shows a specific example of implementation of a graphical user interface implemented by the system shown in FIG. 1 for displaying uterine contraction information in accordance with a specific example of implementation of the invention.

A first specific example of implementation of the graphical user interface module is shown in FIG. 3 of the drawings. In this specific implementation, the first information includes a first tracing 504 conveying rates of uterine contractions over time and the second information includes a second tracing 502 conveying a threshold rate of uterine contractions. The first tracing 504 and the second tracing 502 are displayed in a same viewing window 500. The first tracing 504 conveys a running average of the number of contraction events derived from the contraction signal receiving at input 202 (shown in FIG. 2). In the non-limiting example shown in FIG. 3, the first tracing conveys the number of contraction events over the previous 10 minutes. The threshold rate of uterine contractions illustrated by the second tracing 502 marks a boundary between uterine contraction rates considered to be within safe boundaries (contraction rates falling below the second tracing 502) and contraction rates considered as being associated to riskier situations (contraction rates falling above the second tracing 502). In the example depicted, the second tracing 502 is depicted by a dotted line positioned along a contraction rate of 5 contractions/10 minutes, corresponding to a common definition of uterine hypercontractility. It will be readily appreciated that other suitable threshold rates of uterine contractions may be used without detracting from the spirit of the invention. Advantageously, the implementation depicted in FIG. 3 allows the clinical staff to readily observe the trend in contraction rates over time for a given obstetrics patient as conveyed by the first tracing 504. The first and second tracings 504 502 displayed in a same viewing window 500 allow to clinical staff to readily ascertain the contraction rate and variations thereof with respect to the threshold contraction rate over an extended time period. This allows the clinical staff to have a more complete view of the history of the contraction rate since labour onset, or at least since the clinical staff was monitoring the labour. For example, this allows determining whether the contraction rate is consistently above the threshold rate or whether it was merely a temporary increase in contraction rate and was induced either through the administration of medication or other method. Also, in situations where the contraction rate exceeds the threshold rate, the implementation depicted in FIG. 3 allows the clinical staff to observe by how much the contraction rate exceeds the threshold rate. This may allow the clinical staff to ascertain more easily whether the excess is minor, indicating perhaps a low level risk, or whether it is significant, requiring a quicker intervention.

Figure 4A:
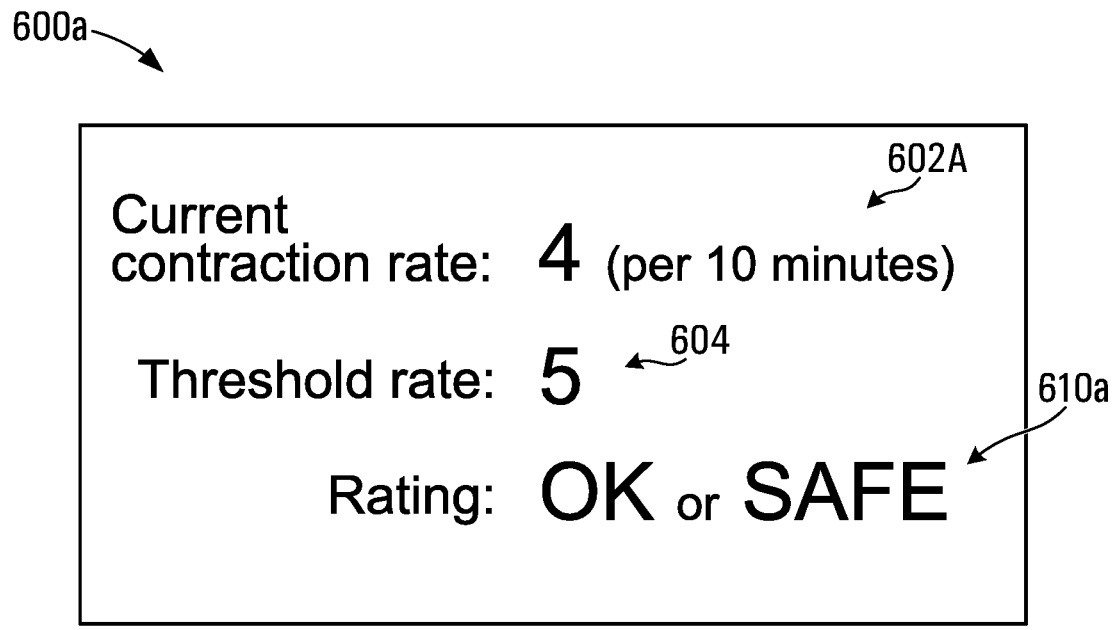
FIGS. 4a and 4b show an alternative specific example of implementation of a graphical user interface implemented by the system shown in FIG. 1 for displaying uterine contraction information in accordance with an alternative specific example of implementation of the invention.
Figure 4B:
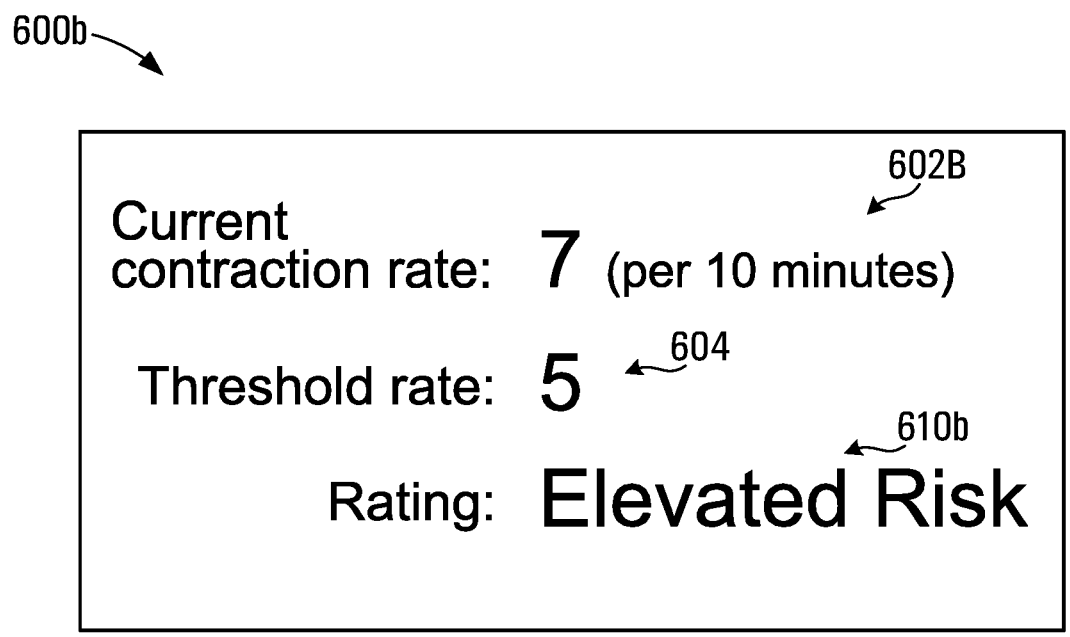

A second specific example of implementation of the graphical user interface module is shown in FIGS. 4a and 4b of the drawings. In the specific implementation shown in FIG. 4a, the first information includes a first alphanumeric element 602a conveying a rate of uterine contractions associated to an obstetrics patient and the second information includes a second alphanumeric element 604 conveying a threshold rate of uterine contractions. The first alphanumeric element 602a and the second alphanumeric element 604 are displayed concurrently in viewing window 600a. In this specific implementation, the first alphanumeric element 602a reflects the current contraction rate derived on the basis of a contraction signal received at input 202 (shown in FIG. 2). In the non-limiting example shown in FIG. 4a, the first alphanumeric element 602a conveys the number of contraction events over the previous 10 minutes. The first alphanumeric element 602a is continuously, or periodically, updated over time on the basis of the contraction signal receiving at input 202 (shown in FIG. 2). The threshold rate of uterine contractions conveyed by the second alphanumeric element 604 indicates the boundary between uterine contraction rates considered to be within safe boundaries and contraction rates considered as being associated to riskier situations. In the example depicted, the second alphanumeric element 604 conveys a contraction rate of 5 contractions/10 minutes, corresponding to a common definition of uterine hypercontractility. It will be readily appreciated that other suitable threshold rates of uterine contractions may be used without detracting from the spirit of the invention.

Advantageously, the implementation depicted in FIGS. 4a and 4b allows the clinical staff to also readily appreciate whether current the contraction rate is within the boundaries of safe care as conveyed by the second alphanumeric element 604.

Optionally, as depicted in the specific examples shown in FIGS. 4a and 4b, the graphical user interface module also displays an alphanumeric indicator 610a in the form of a rating for conveying to the user of the graphical user interface module an indication of whether the current contraction rate is within the boundaries of safe care. In the example depicted in FIG. 4a, the first alphanumeric element 602a conveys a contraction rate of 4 contractions/10 minutes which is below the 5 contractions/10 minutes threshold conveyed by the second alphanumeric element 604. In this case the alphanumeric indicator 610a indicates the message "OK or SAFE" conveying that the current contraction rate is within an acceptable range. In FIG. 4b, the same example of implementation of the graphical user interface module as that shown in FIG. 4a is shown but with a different value of the current contraction rate. In this example, in the viewing window 600b, the first alphanumeric element 602b conveys a contraction rate of 7 contractions/10 minutes, which is above the 5 contractions/10 minutes threshold conveyed by the second alphanumeric element 604. In this case the alphanumeric indicator 610b indicates the message "ELEVATED RISK" conveying that the current contraction rate is not within an acceptable range. In alternative examples of implementation, the alphanumeric indicator 610b may be adapted for displaying graded risk levels such as for example "mildly elevated", "moderately elevated" and "critically elevated" for example.

Alarm Events

The graphical user interface module is adapted for selectively causing an alarm event based at least in part on a rate of uterine contractions and the threshold rate of uterine contractions. In a specific example of implementation, the alarm event is for alerting the clinical staff making use of the system of an occurrence of a potentially problematic situation during labour associated to the occurrence of contractions. The alarm event may be triggered in a number of situations and may be based on rates of uterine contractions and the threshold rate of uterine contractions and optionally on the basis of either one or both of contraction medication information and fetal heart rate information. Examples of the manners in which an alarm event may be selectively caused will be described later on in the specification.

An alarm event, in accordance with a specific example of implementation of the invention, may include one or more components for communicating information to a user of the graphical user interface module.

In a first specific implementation, the alarm event includes displaying a visual indicator to convey to a user of the graphical user interface module an occurrence of a potentially problematic situation during labour. The visual indicator may be displayed as part of the graphical user interface module or in a separate display at a remote location. Any suitable type of visual indicator may be used. Examples of visual indicators that may be used include, without being limited to:

- Variations in color. For example, a color scheme may be established whereby certain colors are associated with varying levels of risk. Portions of the graphical user interface may turn a certain color associated with a high level of risk when, for example, the rate of uterine contractions falls outside a limit set by the threshold rate of uterine contractions. In the non-limiting example depicted in FIG. 3, the portions of the first tracing 504 exceeding the threshold contraction rate (illustrated by reference numeral 508 in the figure) are displayed in a different colour or colour intensity that the remaining portions of the first tracing 504. Alternatively, the entire display window or a portion of the window may be displayed may turn a certain color associated with a high level of risk based at least in part on a rate of uterine contractions conveyed by the first information and the threshold rate of uterine contractions. A non-limiting example of a color scheme is green=normal; yellow: intermediate risk level; red: high level of risk however any suitable color scheme may be used.
- Variation in display intensity of the viewing window. For example, flashing or blinking of the viewing window may be used as a visual indicator to draw the attention of the user;
- Variation in the size or position of the viewing window. For example, the viewing window may be made to appear more prominently on the display unit or at a location that is more likely to draw the attention of the clinical staff;
- Displaying a message prompting/alerting the clinical staff. For example, in FIG. 4b, an alphanumeric message 610 is displayed as "ELEVATED RISK" to convey that the current contraction rate conveyed by the first alphanumeric element 602b has exceeded the threshold rate of uterine contractions conveyed by the second alphanumeric element 604. In this example, when the current contraction rate falls below the threshold rate of uterine contractions, either no message may be displayed or a message conveying that the current contraction rate is within the limit set by the threshold rate of uterine contractions as shown in FIG. 4a.

In a second specific implementation, the alarm event includes causing an audio signal to be issued, alone or in combination with a visual indicator, to draw attention of a user of the graphical user interface module. In this second specific implementation, the processing unit 206 (shown in FIG. 2) releases a signal at the data interface 210 for causing an audio unit (not shown in the figures) to issue an audio signal. The audio unit may be connected directly to the data interface 210 through either a wire-line link or a wireless link. Alternatively, the audio unit may be in communication with the data interface 210 over a network. Alternatively still, the audio unit may be an integral part of apparatus 100.

In a third specific implementation, the alarm event includes causing a message signal to be transmitted to a remote device. The remote device may be, for example, a PDA, telephone, pager or a remote computing terminal. Other suitable types of remote devices may also be envisaged in other specific implementations of the present invention. In this third specific implementation, the processing unit 206 (shown in FIG. 2) releases a signal at the data interface 210 for causing a message signal to be transmitted to the remote device. The remote device may be connected directly to the data interface 210 though either a wire-line link or a wireless link. Alternative, the remote device may be in communication with the data interface 210 over a network.

In a first practical example of interaction, the remote device is a PDA assigned to a doctor responsible for overseeing deliveries in a hospital. At least in part on a rate of uterine contractions conveyed by the first information and the threshold rate of uterine contractions, the graphical user interface module selectively sends a message through the data interface 210 and over a network to the PDA of the doctor to alert that doctor. The message may include any suitable useful information including, but not limited to, the name of the obstetrics patient, the location of the patient, the contraction rate, contraction medication information, fetal heart rate information, labour progression information (duration of labour, time since admission to hospital) and medical history. Optionally, the message may also enable the PDA of the doctor to display all or part of the user interface module described in the present application. For example, the message may enable the PDA of the doctor to display a user interface of the type depicted in FIGS. 3, 4a and 4b. Alternatively, the message may only indicate that a certain patient requires closer monitoring of her contraction rate. The specific format of the message is not critical to the invention and as such will not be discussed further here.

In second practical example of interaction, the remote device is a remote computing terminal located at a centralised nursing station in a hospital birthing centre. At least in part on a rate of uterine contractions conveyed by the first information and the threshold rate of uterine contractions, the graphical user interface module selectively causes a message to be sent to the remote computing terminal. Advantageously, by allowing a message to be transmitted to a remote device, the clinical staff need not be located near the patient or in proximity to the patient to be alerted to potentially problematic situations. In addition, the clinical staff need not be expressly monitoring the progression of the contraction rate to be alerted to an unsafe condition for the contraction rate.

The Process

An exemplary embodiment of the process implemented by the graphical user interface will now be described with reference to FIGS. 6a and 6b.

Figure 6A:
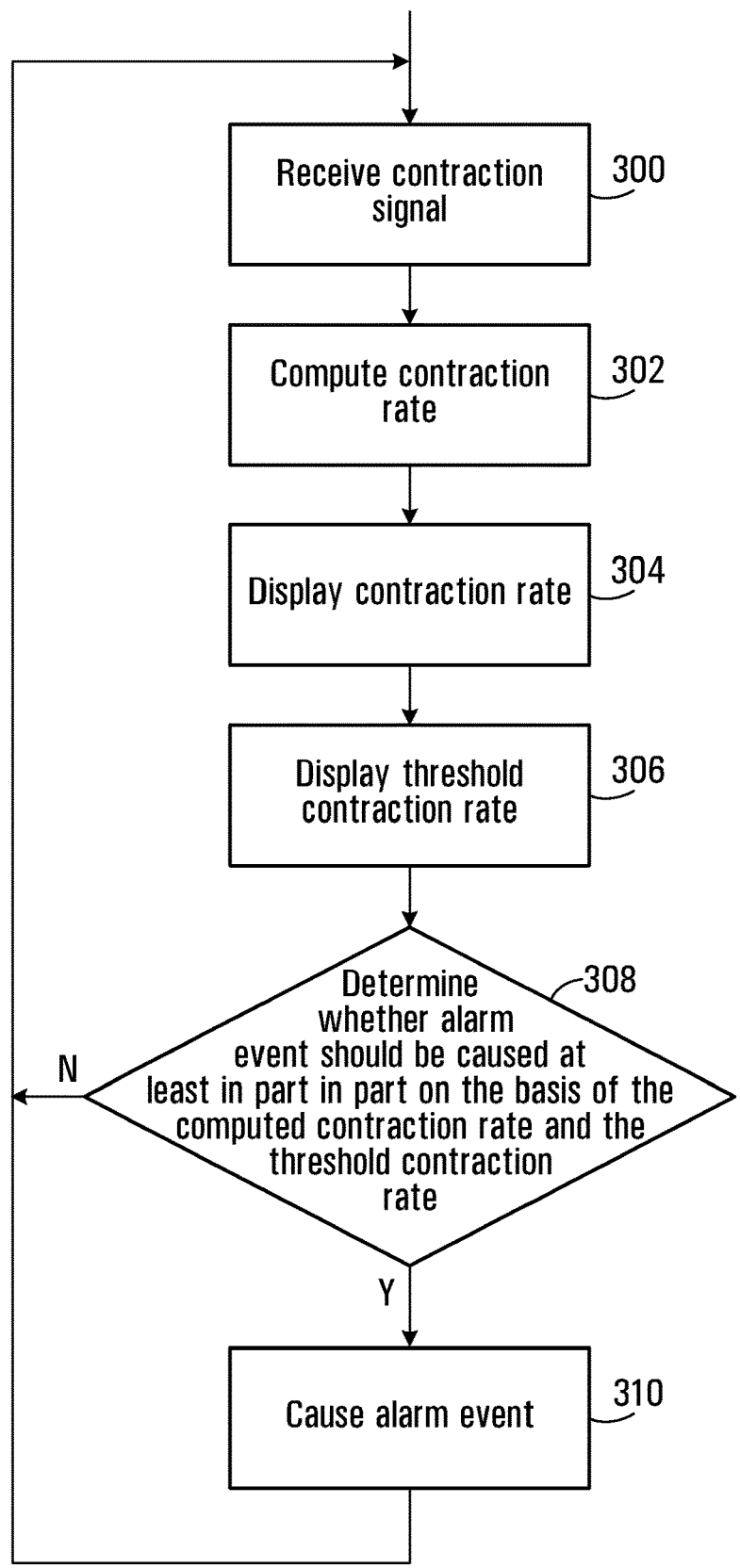
FIGS. 6a and 6b are flow diagrams of a process for displaying uterine contraction information in accordance with a specific example of implementation of the present invention.

With reference to FIG. 6a, at step 300, the contraction signal is received by the graphical user interface module.

At step 302, the graphical user interface module computes a contraction rate on the basis of the contraction signal received at step 300.

Figure 7A:
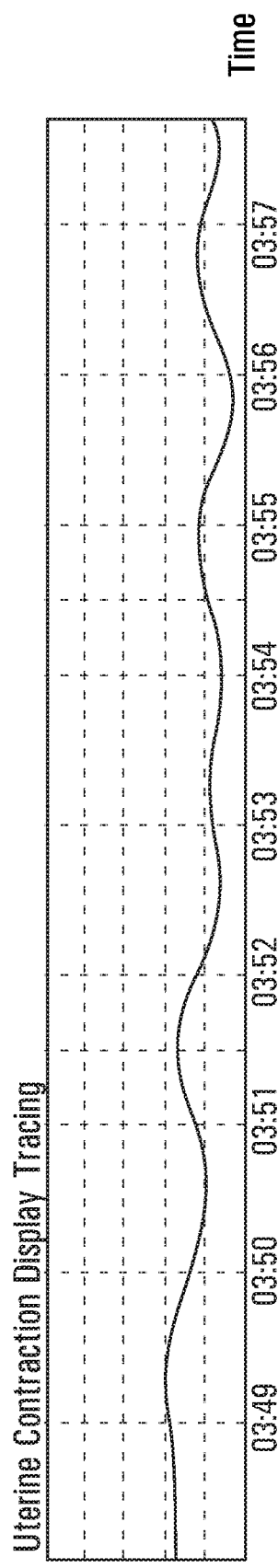
FIGS. 7a and 7b are graphical representations of contraction signals in accordance with non-limiting examples of implementation of the present invention.

The specific manner in which the contraction rate is computed will depend on the format of the contraction signal. In a first specific example, the contraction signal is a continuous signal conveying the intensity of the uterine contractions over time. A non-limiting graphical representation of such a continuous signal is depicted in FIG. 7a for the purpose of illustration. In such an implementation, the graphical user interface module is operative for processing the contraction signal to detect the occurrence of contraction events in the contraction signal. Any suitable pattern recognition technique may be used for identifying the occurrence of contraction events. Such techniques are well known in the art of signal processing and as such will not be described further here. Once the occurrence of contraction events has been detected, the contraction rate can be computed.

Figure 7B:
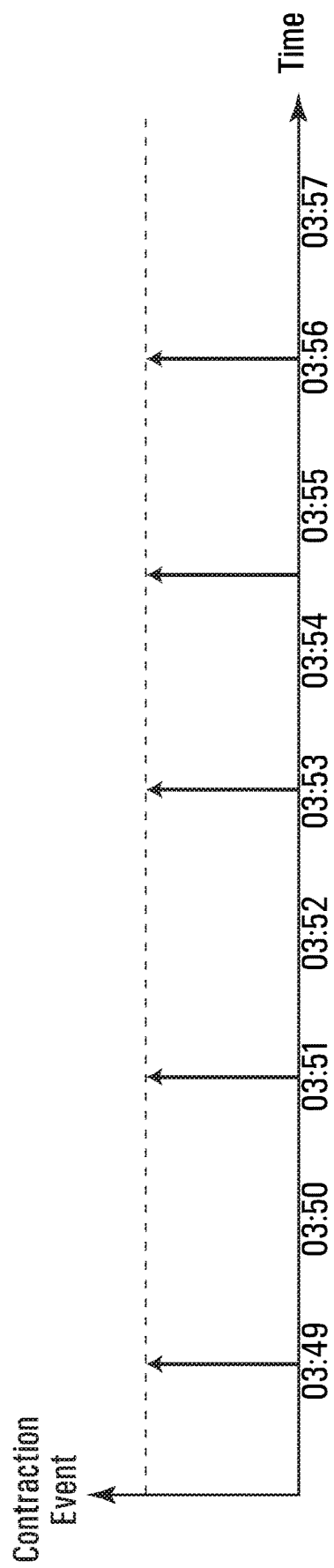

In a second specific example, the contraction signal received at input 202 is comprised of unitary signal events where a signal event is generated when a contraction event is detected. A non-limiting graphical representation of such a continuous signal is depicted in FIG. 7b for the purpose of illustration. In such an implementation, pattern recognition techniques are not required since the presence of contraction events is already conveyed by the contraction signal.

In a specific implementation, the graphical user interface module computes a rate of contraction events in the contraction signal for a certain time segment. The rate of contraction events in the contraction signal may be computed in a number of suitable manners.

In a specific example, a current contraction rate is equal to the number of contraction events detected in the contraction signal over the last time duration T. The duration T may be any suitable time duration. In a non-limiting example, the duration T is 10-15 minutes and the current contraction rate is the number of contraction events in the contraction signal that occurred over the previous 10-15 minutes. Most clinical guidelines describe the desirable contraction frequency based on an observation period of 10-15 minutes. It will be readily apparent to the person skilled in the art that the time duration T may have a duration different than 10-15 minutes. Moreover, the time duration T may be a configurable parameter of the graphical user interface module implemented by processing unit 206 without detracting from the spirit of the invention. Typically, the duration T will be selected to be a time duration sufficiently long so that a few contraction events are likely to occur during active labour but sufficiently short so that the contraction rate for a given time duration T is representative of the progression of the contraction rate during active labour. It will be readily apparent to the person skilled in the art that a very lengthy time duration, let us say 3 hours, does not provide useful information as to whether the contraction rate is within reasonable boundaries. Similarly, a very short time duration, let us say 2 minutes, also does not provide any useful information as to whether the contraction rate is within reasonable boundaries.

It will be readily apparent to the person skilled in the art, in light of the present description, that other well-known techniques for computing a contraction rate on the basis of a contraction signal may be used without detracting from the spirit of the invention.

At step 304, the graphical user interface module implemented by the processing unit 206 displays first information conveying the rate of uterine contractions derived at step 302. At step 306, the graphical user interface module implemented by the processing unit 206 displays concurrently with the first information, second information conveying a threshold rate of uterine contractions. Specific non-limiting examples of formats for the first information and second information were described with reference to FIGS. 3, 4a and 4b of the drawings.

At step 308, the graphical user interface module determines, at least in part on the basis of the computed contraction rate and the threshold contraction rate, whether an alarm event should be caused.

As will become apparent to the person skilled in the art in light of the present specification, different conditions may bring the graphical user interface module to cause an alarm event.

In a first specific example of implementation, an alarm event is triggered depending on the specific circumstances conveyed by the computed contraction rate and the threshold contraction rate alone.

In a second specific example of implementation, an alarm event is triggered depending on the specific circumstances conveyed by the computed contraction rate and the threshold contraction rate in combination with other factors. Such other factors may include, without being limited to, contraction medication information and fetal heart rate information.

In either one of the above described specific examples of implementation, the conditions for causing an alarm event may be determined on the basis of a hospital policy or in accordance with best recognised practices in health care.

In a specific example of implementation, step 308 shown in FIG. 6a includes multiple sub-steps for determining whether an alarm event should be caused. FIG. 6b shows a non-limiting example of implementation of process step 308.

As depicted, at step 350 the graphical user interface module determines whether the computed contraction rate exceeds the limit set by threshold contraction rate. If step 350 is answered in the negative and the computed contraction rate does not exceed the limit set by threshold contraction rate, step 308 determines that no alarm should be caused and the graphical user interface proceeds to step 300.

If step 350 is answered in the affirmative and the computed contraction rate exceeds the limit set by threshold contraction rate, the graphical user interface proceeds to step 352 where an additional condition is tested.

At step 352 the graphical user interface module determines whether the computed contraction rate has exceeded the limit set by the threshold contraction rate for a time duration exceeding a predetermined time duration. This step 352 allows testing whether the excess of the contraction rate is merely transient of whether it is persistent. The predetermined time duration may be established on the basis of a hospital policy or, alternatively, on the basis of other clinical guidelines.

If step 352 is answered in the affirmative and the computed contraction rate exceeds the limit set by threshold contraction rate for a duration of time exceeding the predetermined time duration indicating that the excess of the contraction rate is persistent, step 308 determines that an alarm event should be caused and the graphical user interface proceeds to step 310.

If step 352 is answered in the negative and the computed contraction rate has not exceeded the limit set by threshold contraction rate for a duration of time exceeding the predetermined time duration indicating that the excess of the contraction rate may be transient, the graphical user interface module proceed to step 356 where an additional condition is tested.

At step 356 the graphical user interface module determines whether the contraction medication information indicates that contraction inducing medication was given to the obstetrics patient. Optionally, step 356 may also evaluate the level (or dosage) of contraction inducing medication if any was changed and use that information in effecting the decision step 356.

If step 356 is answered in the affirmative and the contraction medication information indicates that contraction inducing medication was given to the obstetrics patient, step 308 determines that an alarm event should be caused and the graphical user interface proceeds to step 310.

If step 356 is answered in the negative and the contraction medication information indicates that contraction inducing medication was not given to the obstetrics patient, the graphical user interface module proceed to step 358 where an additional condition is tested.

At step 358 the graphical user interface module determines whether the fetal heart rate information available indicates a problematic risk level associated with the baby's well-being. The fetal heart rate information may include a fetal heart rate signal or, alternatively, may include information conveying a level of risk associated with the fetus, the level of risk being derived on the basis of a fetal heart rate signal. In a specific example of implementation, the fetal heart rate information includes a fetal heart rate signal and is received from the fetal heart rate sensor 110 (shown in FIG. 1). Where the fetal heart rate information includes a fetal heart rate signal, step 358 includes processing the signal to determine a level of risk associated with the fetal heart rate signal. Any suitable method for assessing a level of risk on the basis of a fetal heart rate signal may be used. For example, the level of risk may be based on the frequency of the fetal heart rate, whether it is too high or too low for a certain period of time. Alternatively, the level of risk may be based on other suitable known methods. A non-limiting example of a method for providing an indication of the level of risk is described in U.S. Pat. No. 7,113,819, entitled "Method and apparatus for monitoring the condition of a fetus", issued on Sep. 26, 2006 to E. Hamilton et al. and assigned to LMS Medical Systems Ltd. The contents of this document are incorporated herein by reference. Other suitable methods for assessing a level of risk on the basis of a fetal heart rate signal may be used without detracting from the spirit of the invention.

If step 358 is answered in the affirmative and the fetal heart rate information indicates a problematic risk level associated with the baby's well-being, step 308 determines that an alarm event should be caused and the graphical user interface proceeds to step 310.

If step 358 is answered in the negative and the fetal heart rate information does no indicates a problematic risk level associated with the baby's well-being, step 308 determines that no alarm should be caused and the graphical user interface proceeds to step 300.

Figure 6B:
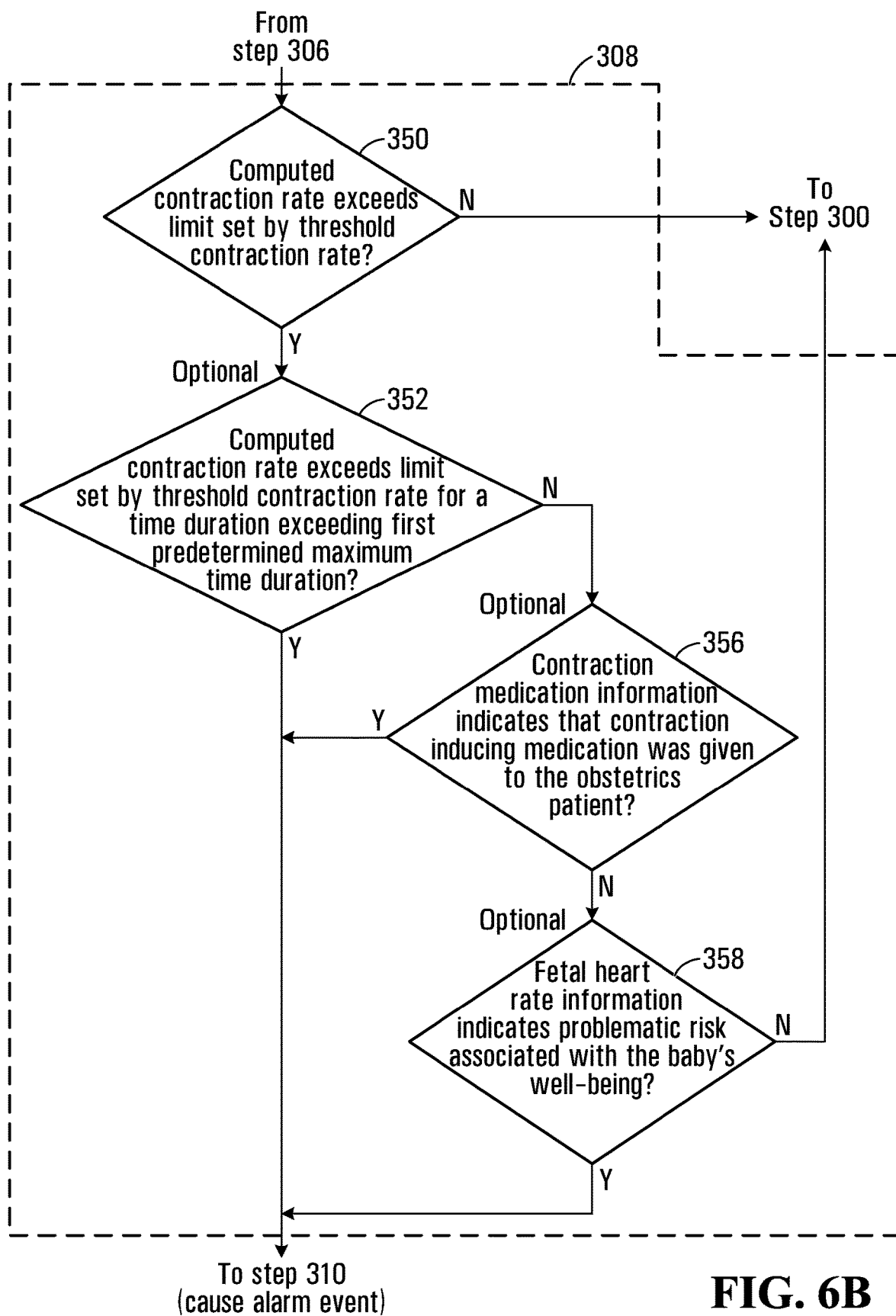

In the specific example of implementation shown in FIG. 6b, steps 352 356 and 358 are optional steps which may be included or omitted from specific implementations of the present invention. In addition, it will be appreciated in light of the present specification that other suitable manners of determining whether an alarm event should be caused on the basis of the computed contraction rate and the threshold contraction rate may be used without detracting from the spirit of the invention. As such, it should be understood that the example depicted in FIG. 6b was presented for the purpose of illustration only.

Returning now to FIG. 6a, if step 308 determines that an alarm event should be caused, the graphical user interface module proceeds to step 310 where an alarm event is triggered. Examples of alarm events were described previously in the specification. The graphical user interface module then returns to step 300 where the next segment of the contraction signal is received and subsequently processed.

If step 308 determines that no alarm event should be caused, the graphical user interface module returns to step 300 where the next segment of the contraction signal is received and subsequently processed.

As can be observed, the process illustrated in FIG. 6a is an iterative process whereby steps 300 to 308 (and selectively step 310 when an alarm event is caused to occur) are repeated as time progresses and as new segments of the contraction signal are received by the apparatus. Over time, the graphical user interface module processes the contraction signal to derive a set of contraction rate data elements, where each contraction rate data element in the set of contraction rate data elements is associated to a segment of the contraction signal. In a non-limiting example, the graphical user interface module computes a running average of contractions in the contraction signal to derive the set of contraction rate data elements.

Although the exemplary embodiment of the process implemented by the graphical user interface described with reference to FIGS. 6a and 6b made reference to a single alarm event presented in box 310, it will be appreciated that different types of alarm events may be caused by the graphical user interface. More specifically, different circumstances conveyed by the computed contraction rate, contraction medication information, fetal heart rate information and optionally other conditions may be associated to respective types of alarm events. Therefore, although the specification described causing a given alarm event, it should be understood that different types of alarm events may be caused and that the type of alarm event caused may be conditioned at least in part on the basis of the circumstances conveyed by the computed contraction rate, (optionally) contraction medication information, (optionally) fetal heart rate information and optionally other conditions Variant As a variant, the graphical user interface module is adapted for displaying, concurrently with the first information conveying a rate of uterine contractions and the second information conveying a threshold rate of uterine contractions, additional information elements related to labour progression.

Figure 5:
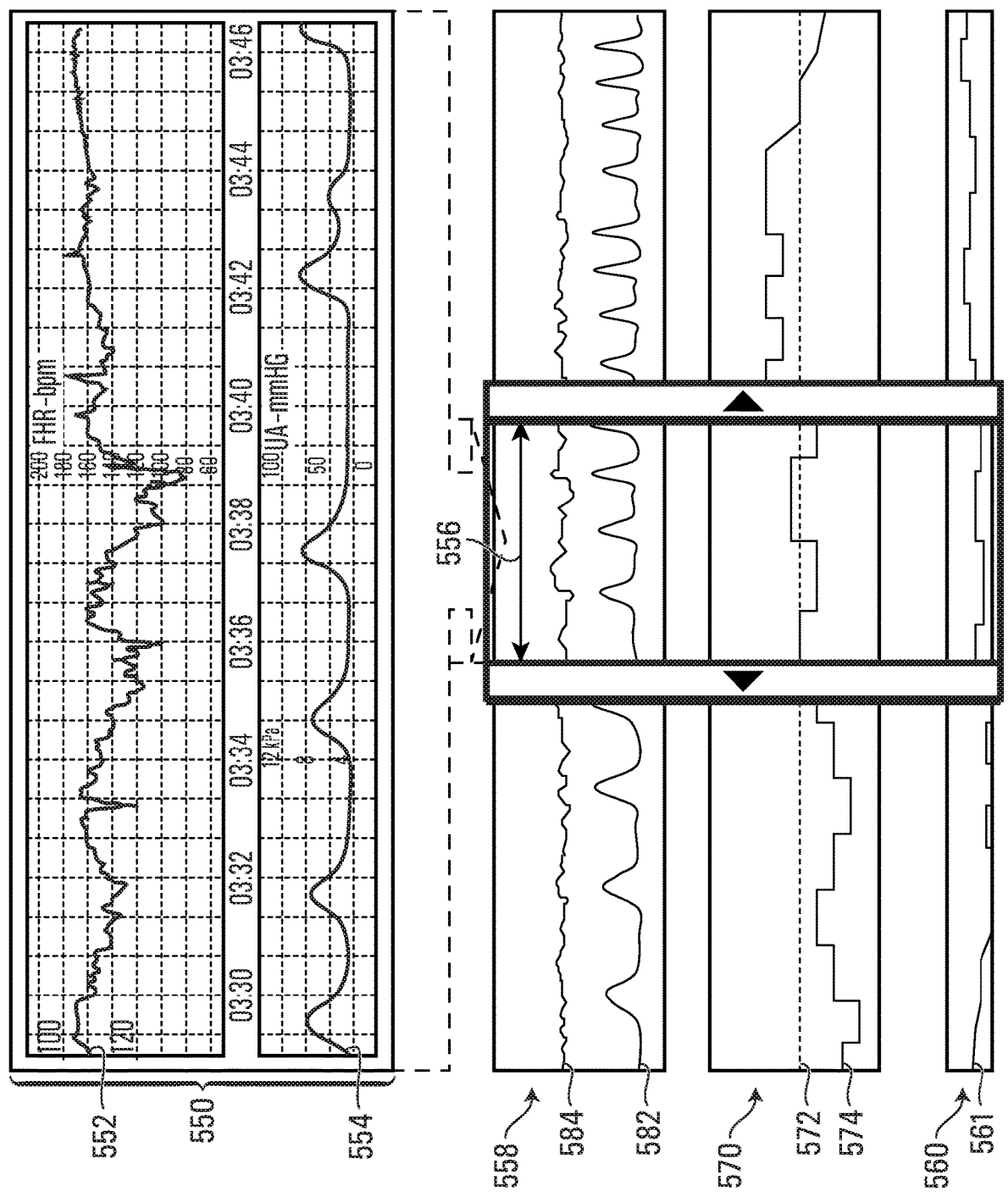
FIG. 5 shows another alternative specific example of implementation of a variant of the graphical user interface implemented by the system shown in FIG. 1 for displaying uterine contraction information in accordance with another specific example of implementation of the invention.

FIG. 5 of the drawings depicts a non-limiting example of implementation of a display generated by the graphical user interface module in accordance with this variant.

As shown, the graphical user interface module displays a first viewing window 570 including a first tracing 574 conveying rates of uterine contractions over time and a second tracing 572 conveying a threshold rate of uterine contractions. The graphical user interface module also displays a second viewing window 558 including a tracing 582 conveying a uterine contraction pattern over time (TOCO tracing) and a tracing 584 conveying a fetal heart rate pattern over time. The tracing 582 conveying a uterine contraction pattern over time is derived on the basis of the contraction signal received from the uterine activity sensor 120 (shown in FIG. 1). The tracing 584 conveying a fetal heart rate pattern over time is derived on the basis of the fetal heart rate signal received from the fetal heart rate sensor 110 (also shown in FIG. 1). Preferably, the first viewing window 570 and second viewing window 558 are time-aligned with one another on the display. In addition, it will be appreciated that either one of the tracings 584 and 582 may be omitted from the second viewing window 558 or that these tracings 584 and 582 may be displayed in separate viewing windows without detracting from the spirit of the invention.

Advantageously, the display of the tracing 584 conveying a fetal heart rate pattern over time allows the users of the system to view a representation of the baby's response to the contraction events.

The display of the tracing 582 conveying a uterine contraction pattern over time allows the users of the system to view a representation of the original contraction signal and to assess whether the tracing 574 conveying rates of uterine contractions over time accurately reflects the rate of contractions in the original contraction signal. This is particularly useful when the contraction signal generated by the uterine activity sensor part of the electronic fetal monitor 110 (shown in FIG. 1) is a continuous contraction signal (as opposed to a unitary contraction signal) since pattern recognition techniques must be used on such a continuous signal to determine the occurrence of a contraction event. These pattern recognition techniques may erroneously detect an occurrence of a contraction event or may fail to detect an occurrence of a contraction event. Therefore, by presenting the user with the tracing 582 conveying a uterine contraction pattern over time, that user may adjust his/her assessment of the first tracing 574.

In the embodiment depicted, the graphical user interface module also displays a control 556 allowing a user to select a portion of the tracings in the first viewing window 570 and/or the second viewing window 558. The user is enabled to manipulate the control 556 by providing signals using user input device 118 (shown in FIG. 1).

In a specific implementation, the control 556 includes a selection box having a transparent portion superposed upon the first viewing window 570 and the second viewing window 558. The portions of the tracings viewable through the transparent portion correspond to the selected portions. The control 556 allows the user to displace and modify the size of the selection box to select a portion of the tracings. Other manners in which portions of a labour progression signal may be selected are described in U.S. Pat. No. 6,907,284 issued to E. Hamilton et al. on Jun. 14, 2005. The contents of this document are incorporated herein by reference.

In the embodiment depicted, the graphical user interface module also displays a third viewing window 550 including a tracing 552 conveying a fetal heart rate pattern over time and a tracing 554 conveying a uterine contraction pattern over time (TOCO tracing). The tracing 552 in the third viewing window 550 conveying a fetal heart rate pattern over time corresponds to the selected portion of the tracing 584 in the second viewing window 558 and is a zoomed-in view of that selected portion. The tracing 554 in the third viewing window 550 conveying a conveying a uterine contraction pattern over time (TOCO tracing) corresponds to the selected portion of the tracing 582 in the second viewing window 558 and is a zoomed-in view of that selected portion. In addition, it will be appreciated that either one of the tracings 552 and 554 may be omitted from the third viewing window 550 or that these tracings 552 and 554 may be displayed in separate viewing windows without detracting from the spirit of the invention.

Advantageously, by displaying zoomed-in views of the selected portions of the tracings 582 and 584, a user will be able to better view responses of the fetal heart rate to individual contraction events (amount of variability size and type of deceleration) and will be able to better assess the intensity and duration of a given contraction event.

In the embodiment depicted, the graphical user interface module also displays a fourth viewing window 560 including a tracing 561 conveying information associated to administration of contraction inducing medication to the obstetrics patient. The tracing 561 is derived on the basis of contraction medication information received by apparatus 100 (shown in FIG. 1). The contraction medication information may indicate whether contraction-inducing medication was administered and, optionally, a dosage of the contraction inducing medication administered. Since, typically, contraction inducing medication is administered continuously over time and not as a one shot dose, the contraction medication information when conveying a dosage of the contraction inducing medication administered may convey such dosage over time. In a first specific example of implementation, the contraction medication information is provided by the clinical staff using user-input device 118. In this first implementation, the clinical staff preferably entered the level (or dosage) of the contraction-inducing medication administered and updates that information when the dosage is modified. In a second specific example of implementation, the contraction medication information is provided automatically by a device, typically in the form of an electronic pump, designed to measure the dosage of medication provided to the obstetrics patient and provide that information over time to apparatus 100. In the embodiment depicted in FIG. 5, the tracing 561 shows the level of medication administered over time to stimulate contractions. It will be appreciated by the person skilled in the art of obstetrics that the tracing 561 is not representative of an actual (real life) situation and that the levels of medication conveyed by tracing 561 are presented here for the purpose of illustration only.

Advantageously, the tracing 561 allows the clinical staff to readily view whether contraction inducing medication was administered to the obstetrics patient being monitored (and optionally the amount of contraction inducing medication which was administered).

Specific Physical Implementation

Those skilled in the art should appreciate that in some embodiments of the invention, all or part of the functionality previously described herein with respect to the apparatus for implementing a user interface for displaying uterine contraction information may be implemented as pre-programmed hardware or firmware elements (e.g., application specific integrated circuits (ASICs), electrically erasable programmable read-only memories (EEPROMs), etc.), or other related components.

In other embodiments of the invention, all or part of the functionality previously described herein with respect to the apparatus for implementing a user interface for displaying uterine contraction information may be implemented as software consisting of a series of instructions for execution by a computing unit. The series of instructions could be stored on a medium which is fixed, tangible and readable directly by the computing unit, (e.g., removable diskette, CD-ROM, ROM, PROM, EPROM or fixed disk), or the instructions could be stored remotely but transmittable to the computing unit via a modem or other interface device (e.g., a communications adapter) connected to a network over a transmission medium. The transmission medium may be either a tangible medium (e.g., optical or analog communications lines) or a medium implemented using wireless techniques (e.g., microwave, infrared or other transmission schemes).

Figure 8:
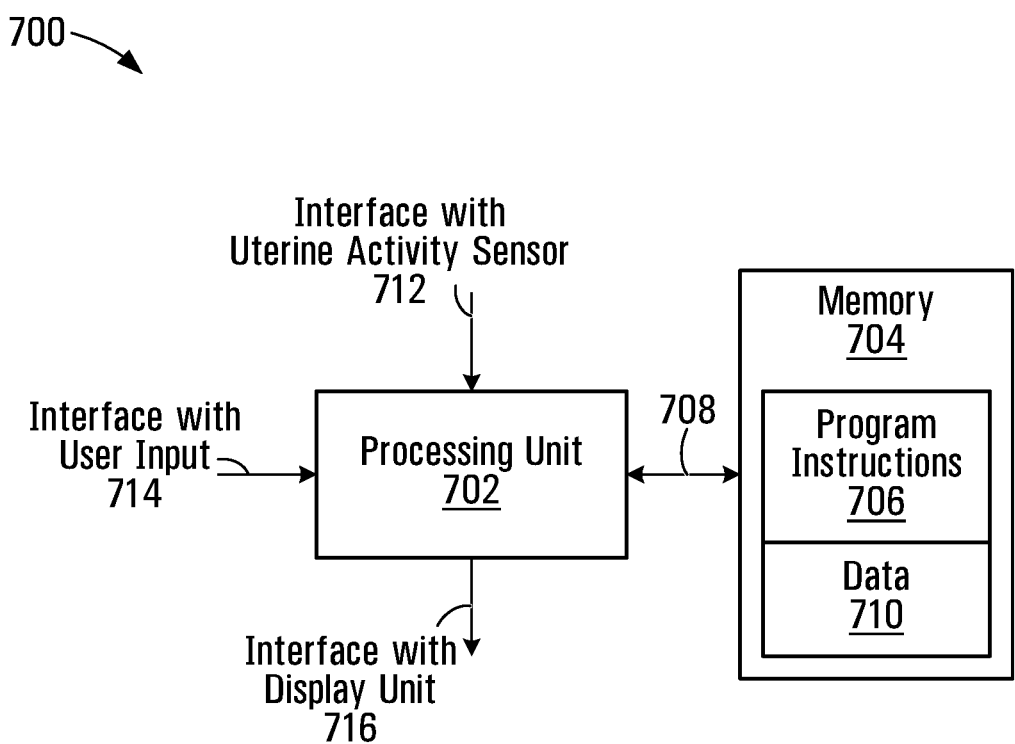
FIG. 8 is a block diagram of an apparatus for providing uterine contraction information in accordance with a specific example of implementation of the present invention.

The apparatus implementing a user interface for displaying uterine contraction information may be configured as a computing unit of the type depicted in FIG. 8, including a processing unit 702 and a memory 704 connected by a communication bus 708. The memory 704 includes data 710 and program instructions 706. In a specific example of implementation, the data 710 stored in memory 704 includes one or more threshold contraction rates. The processing unit 702 is adapted to process the data 710 and the program instructions 706 in order to implement the functional blocks described in the specification and depicted in the drawings. In a non-limiting implementation, the program instructions 706 implement the functionality of processing unit 206 described above. The computing unit 702 may also comprise a number of interfaces 712 714 716 for receiving or sending data elements to external devices. For example, interface 712 is used for receiving data streams indicative of uterine activity and interface 714 is used for receiving a control signals and/or information from the user. Interface 716 is for releasing a signal causing a display unit to display the user interface generated by the program instructions 706. Optionally, the computing unit 702 may include additional interfaces (not shown) for receiving information from additional sensors such as, for example, a fetal heart rate sensor.

Figure 10:
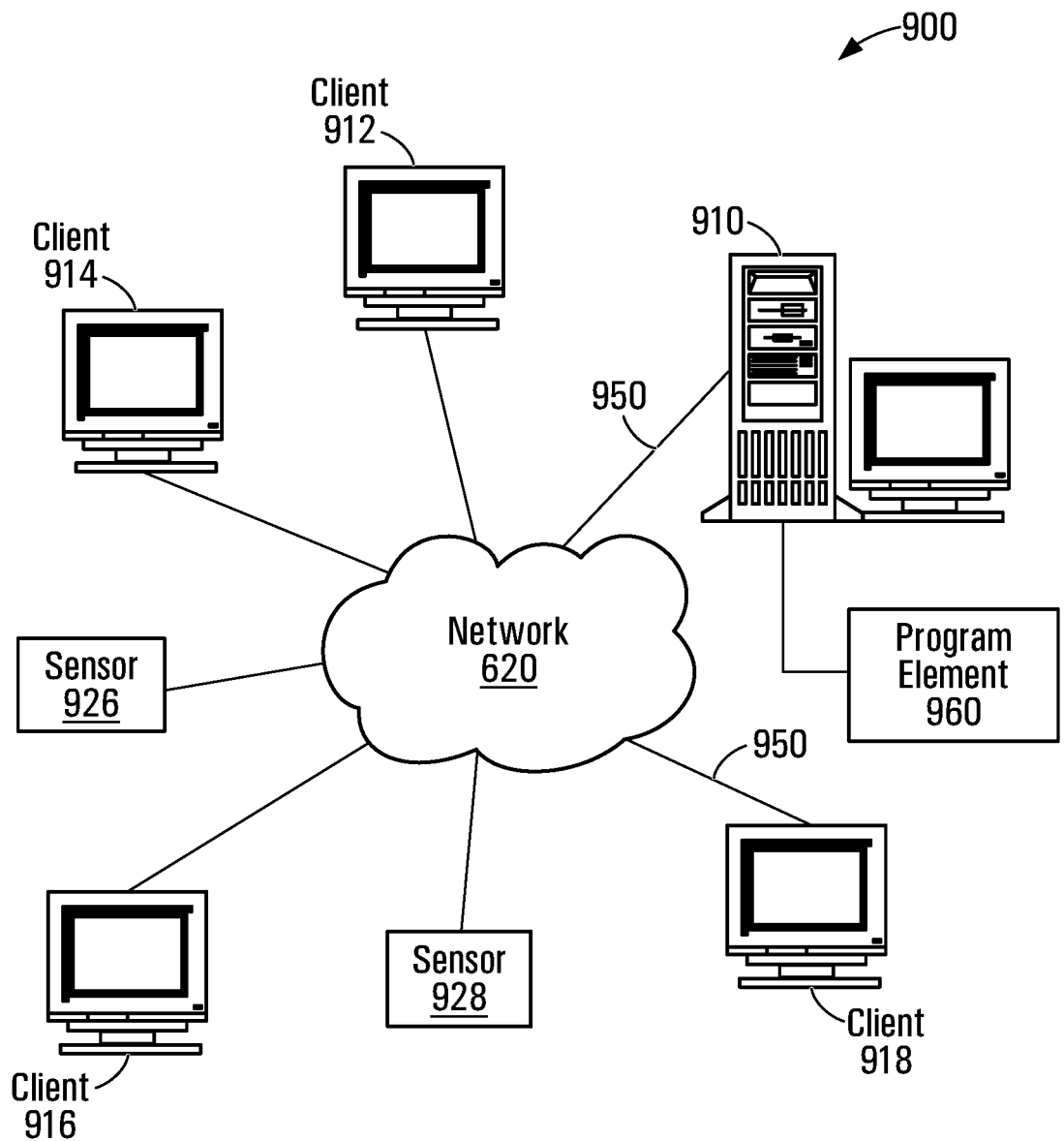
FIG. 10 shows a functional block diagram of a client-server system for providing uterine contraction information in accordance in accordance with an alternative specific non-limiting example of implementation of the present invention.

It will be appreciated that the system for implementing a user interface for displaying uterine contraction information may also be of a distributed nature where the contraction signal is collected at one location by a uterine activity sensor and transmitted over a network to a server unit implementing the graphical user interface. The server unit may then transmit a signal for causing a display unit to display the graphical user interface. The display unit may be located in the same location as the uterine activity sensor, in the same location as the server unit or in yet another location. FIG. 10 illustrates a network-based client-server system 900 for displaying uterine contraction information. The client-server system 900 includes a plurality of client systems 912 914 916 918 connected to a server system 910 through network 920. The communication links 950 between the client systems 912 914 916 918 and the server system 910 can be metallic conductors, optical fibers or wireless, without departing from the spirit of the invention. The network 920 may be any suitable network including but not limited to a global public network such as the Intranet, a private network and a wireless network. The server 910 may be adapted to process and issue signals to display multiple heart rate signals originating from multiple sensors 926 928 concurrently using suitable methods known in the computer related arts.

The server system 910 includes a program element 960 for execution by a CPU. Program element 960 implements similar functionality as program instructions 706 (shown in FIG. 8) and includes the necessary networking functionality to allow the server system 910 to communicate with the client systems 912 914 916 918 over network 920. In a non-limiting implementation, program element 960 includes a number of program element components, each program element components implementing a respective portion of the functionality of the user interface for displaying uterine contraction information.

Figure 9:
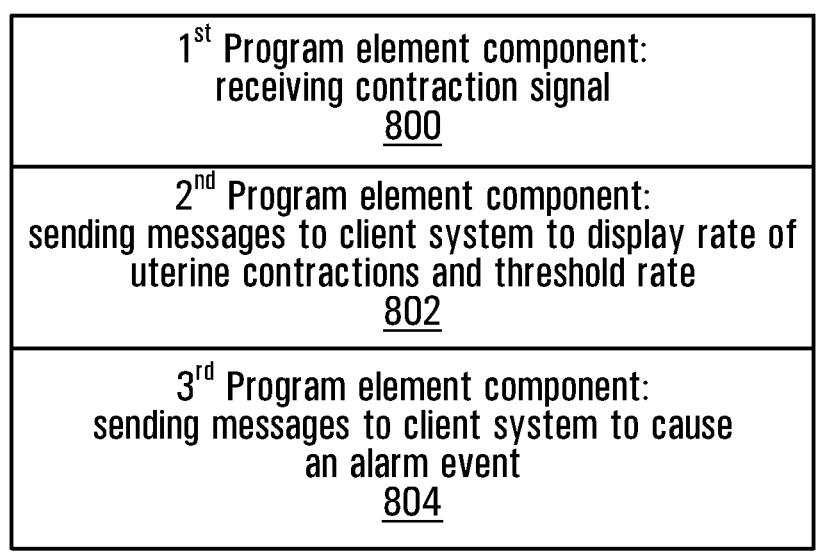
FIG. 9 is a high level conceptual block diagram of a program element for implementing a graphical user interface of the type shown in either one of FIGS. 3, 4a, 4b and 5 in accordance with a specific example of implementation of the present invention.

FIG. 9 shows a non-limiting example of the architecture of program element 960 at the server system. As shown, the program element 960 includes three program element components:

1. the first program element component 800 is executed on server system 910 and is for receiving a contraction signal conveying information related to occurrences of uterine contractions over time;
2. the second program element component 802 is executed on server system 910 and is for sending messages to a client system, say client system 914, for causing client system 914 to:
    display first information conveying a rate of uterine contractions, the first information being derived at least in part on the basis of at least a portion of the contraction signal; and
    display, concurrently with the first information, second information conveying a threshold rate of uterine contractions;
3. the third program element component 804 is executed on server system 910 and is for selectively sending messages to client system 914 for causing an alarm event based at least in part on a rate of uterine contractions conveyed by said first information and the threshold rate of uterine contractions. Alternatively, the third program element component 804 is executed on server system 910 and is for selectively sending messages to a client system distinct from the client system 914 for causing an alarm event at the distinct client system. The messages for causing an alarm event may include alarm program elements for execution at the client system, the alarm program elements implementing the alarm events when executed at the client system. Alternatively, alarm program elements for implementing the alarm events are stored at the client system and the messages for causing an alarm event transmitted from the server system 910 include instructions for causing the alarm program elements at the client system to be executed.

Those skilled in the art should further appreciate that the program instructions 706 and 960 may be written in a number of programming languages for use with many computer architectures or operating systems. For example, some embodiments may be implemented in a procedural programming language (e.g., "C") or an object oriented programming language (e.g., "C++" or "JAVA").

Although the present invention has been described in considerable detail with reference to certain preferred embodiments thereof, variations and refinements are possible without departing from the spirit of the invention. Therefore, the scope of the invention should be limited only by the appended claims and their equivalents.

The invention claimed is:

1. An apparatus for monitoring an obstetrics patient during labour, said apparatus comprising:
    (a) an input for receiving a contraction signal associated with the obstetrics patient, the contraction signal conveying information related to occurrences of uterine contractions over time;
    (b) a processing unit in communication with said input, said processing unit being programmed for:
        (i) processing the contraction signal to derive a sequence of rates of uterine contractions over time;
        (ii) implementing a Graphical User Interface (GUI) presenting:
            (1) a first viewing window displaying:
                (a) a first tracing of at least part of the sequence of rates of uterine contractions over time;
                (b) information conveying a threshold rate of uterine contractions;
        (iii) dynamically adapting the GUI over time to shown updated versions of the first tracing in the first viewing window based on the contraction signal received at the input;
        (iv) processing the sequence of rates of uterine contractions derived over time to:
            (1) detect occurrences of anomalous contraction rates in said sequence of rates of uterine contractions over time at least in part by processing the rates of uterine contractions in said sequence of rates of uterine contractions to identify specific rates of uterine contractions in said sequence that have fallen outside a limit set by the threshold rate of contraction; and (2) processing the detected occurrences of anomalous contraction rates to identify one or more portions of the first tracing corresponding to sustained anomalous contraction rate segments during which anomalous contraction rates have persisted for time durations exceeding a predetermined time duration;

(v) in response to identification of a specific sustained anomalous contraction rate segment, causing the GUI to trigger an alarm event including the display of a visual indicator to attract attention of clinical staff to a specific portion of the first tracing displayed in the first viewing window, wherein the specific portion of the first tracing corresponds to the identified specific sustained anomalous contraction rate segment during which anomalous contraction rates have persisted.

2. A non-transitory computer readable storage medium storing a program element suitable for execution by a processor, said program element implementing a process for monitoring an obstetrics patient during labour, said processor when executing said program element being configured for:

(a) receiving a contraction signal associated with the obstetrics patient, the contraction signal conveying information related to uterine contractions over time;

(b) processing the contraction signal to derive a sequence of rates of uterine contractions over time;

(c) directing the processor to implement a Graphical User Interface (GUI) presenting:

(i) a first viewing window displaying:

(1) a first tracing conveying at least part of the sequence of rates of uterine contractions over time;

(2) a second tracing conveying a threshold rate of uterine contractions;

(ii) a second viewing window presented with said first viewing window and displaying a third tracing conveying measurements of uterine pressure over a first time segment, said third tracing being derived at least in part by processing said contraction signal;

(iii) a third viewing window presented with said first viewing window and said second viewing window, said third viewing window displaying a zoomed-in portion of the third tracing displayed in the second viewing window;

(iv) a user operable control configured for accepting a user selection conveying a selected portion of the third tracing, the selected portion of the third tracing conveying measurements of uterine pressure over a sub-segment of the first time segment;

(d) in response to receipt of a user selection made through the user operable control and conveying a specific portion of the third tracing, directing the processor to dynamically adapt the GUI to cause the zoomed-in portion of the third tracing displayed in the third viewing window to convey measurements of uterine pressure over the specific portion of the third tracing conveyed by the user selection;

(e) processing the sequence of rates of uterine contractions derived over time to:

(i) detect occurrences of anomalous contraction rates in said sequence of rates of uterine contractions over time at least in part by processing the rates of uterine contractions in said sequence of rates of uterine contractions to identify specific rates of uterine contractions in said sequence that have fallen outside a limit set by the threshold rate of contraction; and (ii) processing the detected occurrences of anomalous contraction rates to identify one or more portions of the first tracing corresponding to sustained anomalous contraction rate segments during which anomalous contraction rates have persisted for time durations exceeding a predetermined time duration;

(f) causing the GUI to trigger an alarm event to attract attention of clinical staff to a specific portion of the first tracing displayed in the first viewing window at least in part in response to identification of a specific sustained anomalous contraction rate segment, wherein the specific portion of the first tracing corresponds to the identified specific sustained anomalous contraction rate segment.

3. A non-transitory computer readable storage medium as defined in claim 2, said processor when executing said program element being adapted for:

(a) receiving contraction medication information conveying whether contraction inducing medication was administered to the obstetrics patient;

(b) causing the GUI to trigger the alarm event to attract attention of clinical staff:

(i) in response to identification of a specific sustained anomalous contraction rate segment; and (ii) based on said contraction medication information.

4. A non-transitory computer readable storage medium as defined in claim 2, said processor when executing said program element being adapted for:

(a) receiving fetal heart rate information;

(b) causing the GUI to trigger the alarm event to attract attention of clinical staff:

(i) in response to identification of a specific sustained anomalous contraction rate segment; and (ii) based on said fetal heart rate information.

5. A non-transitory computer readable storage medium as defined in claim 2, said processor when executing said program element being adapted for:

(a) receiving fetal heart rate information;

(b) receiving contraction medication information conveying whether contraction inducing medication was administered to the obstetrics patient;

(c) causing the GUI to trigger the alarm event to attract attention of clinical staff:

(i) in response to identification of a specific sustained anomalous contraction rate segment;

(ii) based on said contraction medication information; and (iii) based on said fetal heart rate information.

6. A non-transitory computer readable storage medium as described in claim 2, wherein said alarm event includes displaying a visual indicator.

7. A non-transitory computer readable storage medium as described in claim 2, wherein said alarm event includes causing an audio signal to be issued.

8. A non-transitory computer readable storage medium as described in claim 2, wherein said alarm event includes causing a message signal to be transmitted to a remote device.

9. A non-transitory computer readable storage medium as described in claim 8, wherein the remote device is a device selected from the set consisting of a PDA, telephone, pager and computing terminal.

10. A non-transitory computer readable storage medium as described in claim 8, wherein said alarm event includes causing a message signal to be transmitted over a network to the remote device.

11. A non-transitory computer readable storage medium as defined in claim 2, wherein said user operable control includes a selection box.

12. A computer readable storage medium as defined in claim 11, wherein said selection box includes a transparent portion, said selection box being superposed upon said second viewing window.

13. An apparatus for monitoring an obstetrics patient during labour, said apparatus comprising:
 (a) an input for receiving a contraction signal associated with the obstetrics patient, the contraction signal conveying information related to occurrences of uterine contractions over time;
 (b) a processing unit in communication with said input, said processing unit being programmed for:
  (i) processing the contraction signal to derive a sequence of rates of uterine contractions over time;
  (ii) implementing a Graphical User Interface (GUI) presenting:
   (1) a first viewing window displaying:
    (a) a first tracing conveying at least part of the sequence of rates of uterine contractions over time;
    (b) a second tracing conveying a threshold rate of uterine contractions;
   (2) a second viewing window presented with said first viewing window and displaying a third tracing conveying measurements of uterine pressure over a first time segment, said third tracing being derived at least in part by processing said contraction signal;
   (3) a third viewing window presented with said first viewing window and said second viewing window, said third viewing window displaying a zoomed-in portion of the third tracing displayed the second viewing window;
   (4) a user operable control configured for accepting a user selection conveying a selected portion of the third tracing, the selected portion of the third tracing conveying measurements of uterine pressure over a sub-segment of the first time segment;
  (iii) in response to receipt of a user selection conveying a specific portion of the third tracing, dynamically adapting the GUI to cause the zoomed-in portion of the third tracing displayed in the third viewing window to convey measurements of uterine pressure over the specific portion of the third tracing conveyed by the user selection;
  (iv) processing the sequence of rates of uterine contractions derived over time to:
   (1) detect occurrences of anomalous contraction rates in said sequence of rates of uterine contractions over time at least in part by processing the rates of uterine contractions in said sequence of rates of uterine contractions over time to identify specific rates of uterine contractions in said sequence that have fallen outside a limit set by the threshold rate of contraction; and
   (2) processing the detected occurrences of anomalous contraction rates to identify one or more portions of the first tracing corresponding to sustained anomalous contraction rate segments during which anomalous contraction rates have persisted for time durations exceeding a predetermined time duration;
  (v) causing the GUI to trigger an alarm event to attract attention of clinical staff to a specific portion of the first tracing displayed in the first viewing window at least in part in response to identification of a specific sustained anomalous contraction rate segment, wherein the specific portion of the first tracing corresponds to the identified specific sustained anomalous contraction rate segment.

14. An apparatus as defined in claim 13, said processing unit being programmed for:
 (a) receiving contraction medication information conveying whether contraction inducing medication was administered to the obstetrics patient;
 (b) causing the GUI to trigger the alarm event to attract attention of clinical staff:
  (i) in response to identification of a specific sustained anomalous contraction rate segment; and
  (ii) based on said contraction medication information.

15. An apparatus as defined in claim 13, said processing unit being programmed for:
 (a) receiving fetal heart rate information;
 (b) causing the GUI to trigger the alarm event to attract attention of clinical staff:
  (i) in response to identification of a specific sustained anomalous contraction rate segment; and
  (ii) based on said fetal heart rate information.

16. An apparatus as defined in claim 13, said processing unit being programmed for:
 (a) receiving fetal heart rate information;
 (b) receiving contraction medication information conveying whether contraction inducing medication was administered to the obstetrics patient;
 (c) causing the GUI to trigger the alarm event to attract attention of clinical staff:
  (i) in response to identification of a specific sustained anomalous contraction rate segment;
  (ii) based on said contraction medication information; and
  (iii) based on said fetal heart rate information.

17. An apparatus as described in claim 13, wherein said alarm event includes displaying a visual indicator.

18. An apparatus as described in claim 13, wherein said alarm event includes causing an audio signal to be issued.

19. An apparatus as described in claim 13, wherein said alarm event includes causing a message signal to be transmitted to a remote device.

20. An apparatus as described in claim 19, wherein the remote device is a device selected from the set consisting of a PDA, telephone, pager and computing terminal.

21. An apparatus as described in claim 19, wherein said alarm event includes causing a message signal to be transmitted over a network to the remote device.

22. An apparatus as defined in claim 13, wherein said user operable control includes a selection box.

23. An apparatus as defined in claim 22, wherein said selection box includes a transparent portion, said selection box being superposed upon said second viewing window.

24. A method for monitoring an obstetrics patient during labour, said method comprising:
 (a) receiving at an input of a computing apparatus having a processor a contraction signal associated with the obstetrics patient, said contraction signal conveying information related to occurrences of uterine contractions over time;

(b) using the processor of the computing apparatus:
  (i) processing the contraction signal to derive a sequence of rates of uterine contractions over time;
  (ii) implementing a Graphical User Interface (GUI) presenting:
    (1) a first viewing window displaying:
      (a) a first tracing conveying at least part of the sequence of rates of uterine contractions over time;
      (b) a second tracing conveying a threshold rate of uterine contractions;
    (2) a second viewing window presented with said first viewing window and displaying a third tracing conveying measurements of uterine pressure over a first time segment, said third tracing being derived at least in part by processing said contraction signal;
    (3) a third viewing window presented with said first viewing window and said second viewing window, said third viewing window displaying a zoomed-in portion of the third tracing displayed the second viewing window;
    (4) a user operable control configured for accepting a user selection conveying a selected portion of the third tracing, the selected portion of the third tracing conveying measurements of uterine pressure over a sub-segment of the first time segment;
  (iii) in response to receipt of a user selection conveying a specific portion of the third tracing, dynamically adapting the GUI to cause the zoomed-in portion of the third tracing displayed in the third viewing window to convey measurements of uterine pressure over the specific portion of the third tracing conveyed by the user selection;
  (iv) processing the sequence of rates of uterine contractions derived over time to:
    (1) detect occurrences of anomalous contraction rates in said sequence of rates of uterine contractions over time at least in part by processing the rates of uterine contractions in said sequence of rates of uterine contractions over time to identify specific rates of uterine contractions in said sequence that have fallen outside a limit set by the threshold rate of contraction; and
    (2) processing the detected occurrences of anomalous contraction rates to identify one or more portions of the first tracing corresponding to sustained anomalous contraction rate segments during which anomalous contraction rates have persisted for time durations exceeding a predetermined time duration;
  (v) causing the GUI to trigger an alarm event to attract attention of clinical staff to a specific portion of the first tracing displayed in the first viewing window at least in part in response to identification of a specific sustained anomalous contraction rate segment, wherein the specific portion of the first tracing corresponds to the identified specific sustained anomalous contraction rate segment.

25. A method as defined in claim 24, said method comprising:
(a) receiving contraction medication information conveying whether contraction inducing medication was administered to the obstetrics patient;
(b) causing the GUI to trigger the alarm event to attract attention of clinical staff:
  (i) in response to identification of a specific sustained anomalous contraction rate segment; and
  (ii) based on said contraction medication information.

26. A method as defined in claim 24, said method comprising:
(a) receiving fetal heart rate information;
(b) causing the GUI to trigger the alarm event to attract attention of clinical staff:
  (i) in response to identification of a specific sustained anomalous contraction rate segment; and
  (ii) based on said fetal heart rate information.

27. A method as defined in claim 24, said method comprising:
(a) receiving fetal heart rate information;
(b) receiving contraction medication information conveying whether contraction inducing medication was administered to the obstetrics patient;
(c) causing the GUI to trigger the alarm event to attract attention of clinical staff:
  (i) in response to identification of a specific sustained anomalous contraction rate segment; and
  (ii) based on said contraction medication information; and
  (iii) based on said fetal heart rate information.

28. A method as described in claim 24, wherein said alarm event includes displaying a visual indicator.

29. A method as described in claim 24, wherein said alarm event includes causing an audio signal to be issued.

30. A method as described in claim 24, wherein said alarm event includes causing a message signal to be transmitted to a remote device.

31. A method as described in claim 30, wherein the remote device is a device selected from the set consisting of a PDA, telephone, pager and computing terminal.

32. A method as described in claim 24, wherein said alarm event includes causing a message signal to be transmitted over a network to the remote device.

33. A method as defined in claim 24, wherein said user operable control includes a selection box.

34. A method as defined in claim 33, wherein said selection box includes a transparent portion, said selection box being superposed upon said second viewing window.

35. A labour monitoring system comprising:
(a) a sensor for receiving information indicative of occurrences of uterine contractions over time;
(b) a display device;
(c) an apparatus for monitoring an obstetrics patient during labour, said apparatus comprising:
  (i) an input in communication with said sensor for receiving a contraction signal associated with the obstetrics patient, said contraction signal conveying information related to occurrences of uterine contractions over time;
  (ii) a processing unit in communication with said input and with said display device, said processing unit being programmed for:
    (1) processing the contraction signal to derive a sequence of rates of uterine contractions over time;
    (2) implementing a Graphical User Interface (GUI) presenting:
      (a) a first viewing window displaying:
        (i) a first tracing conveying at least part of the sequence of rates of uterine contractions over time;

(ii) a second tracing conveying a threshold rate of uterine contractions;

(b) a second viewing window presented with said first viewing window and displaying a third tracing conveying measurements of uterine pressure over a first time segment, said third tracing being derived at least in part by processing said contraction signal;

(c) a third viewing window presented with said first viewing window and said second viewing window, said third viewing window displaying a zoomed-in portion of the third tracing displayed the second viewing window;

(d) a user operable control configured for accepting a user selection conveying a selected portion of the third tracing, the selected portion of the third tracing conveying measurements of uterine pressure over a sub-segment of the first time segment;

(3) in response to receipt of a user selection conveying a specific portion of the third tracing, dynamically adapting the GUI to cause the zoomed-in portion of the third tracing displayed in the third viewing window to convey measurements of uterine pressure over the specific portion of the third tracing conveyed by the user selection;

(4) processing the sequence of rates of uterine contractions derived over time to:

(a) detect occurrences of anomalous contraction rates in said sequence of rates of uterine contractions over time at least in part by processing the rates of uterine contractions in said sequence of rates of uterine contractions over time to identify specific rates of uterine contractions in said sequence that have fallen outside a limit set by the threshold rate of contraction; and (b) processing the detected occurrences of anomalous contraction rates to identify one or more portions of the first tracing corresponding to sustained anomalous contraction rate segments during which anomalous contraction rates have persisted for time durations exceeding a predetermined time duration;

(5) causing the GUI to trigger an alarm event to attract attention of clinical staff to a specific portion of the first tracing displayed in the first viewing window at least in part in response to identification of a specific sustained anomalous contraction rate segment, wherein the specific portion of the first tracing corresponds to the identified specific sustained anomalous contraction rate segment;

(iii) an output in communication with said processing unit, said output being suitable for releasing a display signal for causing the GUI to be displayed on the display device.

36. A labour monitoring system as described in claim 35, wherein said alarm event includes displaying a visual indicator.

37. A labour monitoring system as described in claim 35, wherein said alarm event includes causing an audio signal to be issued.

38. A labour monitoring system as described in claim 35, wherein said alarm event includes causing a message signal to be transmitted to a remote device.

* * * * *